(12) United States Patent
Parker et al.

(10) Patent No.: US 8,897,888 B2
(45) Date of Patent: *Nov. 25, 2014

(54) KNITTED ELECTRODE ASSEMBLY AND INTEGRATED CONNECTOR FOR AN ACTIVE IMPLANTABLE MEDICAL DEVICE

(75) Inventors: John L. Parker, Roseville (AU); David Robinson, Bronte (AU)

(73) Assignee: Saluda Medical Pty Limited, Eveleigh, NSW (AU)

( * ) Notice: Subject to any disclaimer, the term of this patent is extended or adjusted under 35 U.S.C. 154(b) by 950 days.

This patent is subject to a terminal disclaimer.

(21) Appl. No.: 12/549,457

(22) Filed: Aug. 28, 2009

(65) Prior Publication Data

US 2010/0070007 A1 Mar. 18, 2010

(30) Foreign Application Priority Data

Sep. 17, 2008 (AU) ................................ 2008904838
Apr. 8, 2009 (AU) ................................ 2009901531
Apr. 8, 2009 (AU) ................................ 2009901534

(51) Int. Cl.
*A61N 1/05* (2006.01)
*A61M 25/00* (2006.01)
*A61N 1/375* (2006.01)

(52) U.S. Cl.
CPC ......... *A61N 1/0529* (2013.01); *A61M 25/0009* (2013.01); *A61N 1/375* (2013.01)
USPC ............ 607/116; 600/372; 600/395; 181/229

(58) Field of Classification Search
CPC ..... A61N 1/05; A61N 1/0472; A61N 1/0484; A61B 2562/125

USPC .................... 181/229; 600/372, 395; 607/116
See application file for complete search history.

(56) References Cited

U.S. PATENT DOCUMENTS

| | | | |
|---|---|---|---|
| 3,773,034 A | 11/1973 | Burns et al. | |
| 4,239,046 A | 12/1980 | Ong | |
| 4,411,276 A | 10/1983 | Dickhudt et al. | |
| 4,411,277 A | 10/1983 | Dickhudt | |
| 4,437,109 A | 3/1984 | Anthony et al. | |
| 4,543,090 A | 9/1985 | McCoy | |
| 4,549,556 A | 10/1985 | Tarjan et al. | |
| 4,708,149 A | 11/1987 | Axelgaard et al. | |
| 5,102,727 A * | 4/1992 | Pittman et al. | 442/187 |
| 5,300,110 A | 4/1994 | Latterell et al. | |
| 5,314,451 A | 5/1994 | Mulier | |

(Continued)

FOREIGN PATENT DOCUMENTS

EP 1 923 967 5/2008

OTHER PUBLICATIONS

PCT International Search Report, PCT/US2009/055392, prepared Nov. 19, 2009; 4 pgs.

*Primary Examiner* — Niketa Patel
*Assistant Examiner* — Christopher A Flory

(57) ABSTRACT

An active implantable medical device (AIMD). The AIMD comprises: a knitted electrode assembly comprising: at least one biocompatible, electrically non-conductive filament arranged in substantially parallel rows each stitched to an adjacent row, and at least one biocompatible, electrically conductive filament having a first end intertwined with a first row of the at least one non-conductive filament, and a second end intertwined with a second row of the at least one non-conductive filament, wherein the first and second rows are spaced from one another.

9 Claims, 20 Drawing Sheets

(56) References Cited

U.S. PATENT DOCUMENTS

| | | |
|---|---|---|
| 5,466,252 A | 11/1995 | Soukup et al. |
| 5,604,976 A | 2/1997 | Stobie et al. |
| 5,679,026 A | 10/1997 | Fain et al. |
| 5,720,099 A | 2/1998 | Parker et al. |
| 6,198,969 B1 | 3/2001 | Kuzma |
| 6,210,771 B1 * | 4/2001 | Post et al. ............... 428/100 |
| 6,321,126 B1 | 11/2001 | Kuzma |
| 6,381,482 B1 * | 4/2002 | Jayaraman et al. .......... 600/388 |
| 6,421,569 B1 | 7/2002 | Treaba et al. |
| 6,649,886 B1 * | 11/2003 | Kleshchik ............... 219/529 |
| 6,662,035 B2 | 12/2003 | Sochor |
| 2003/0186608 A1 * | 10/2003 | Goldberg ............... 442/304 |
| 2003/0212319 A1 | 11/2003 | Magill |
| 2004/0237494 A1 | 12/2004 | Karayianni et al. |
| 2005/0165464 A1 | 7/2005 | Parker et al. |
| 2006/0106459 A1 | 5/2006 | Truckai et al. |
| 2006/0218778 A1 * | 10/2006 | Jawahar et al. ............ 29/605 |
| 2006/0265049 A1 * | 11/2006 | Gray et al. ............... 623/1.16 |
| 2006/0280322 A1 * | 12/2006 | Abe ..................... 381/300 |
| 2006/0281382 A1 * | 12/2006 | Karayianni et al. ......... 442/181 |
| 2007/0112344 A1 * | 5/2007 | Keilman .................. 606/41 |
| 2007/0190881 A1 * | 8/2007 | Shibaoka et al. ............ 442/228 |
| 2007/0202728 A1 | 8/2007 | Olson et al. |
| 2007/0251082 A1 | 11/2007 | Milojevic et al. |
| 2008/0147155 A1 * | 6/2008 | Swoyer et al. ............. 607/116 |
| 2009/0099441 A1 * | 4/2009 | Giszter et al. ............. 600/377 |
| 2009/0159149 A1 * | 6/2009 | Karayianni et al. ...... 139/425 R |
| 2010/0069835 A1 * | 3/2010 | Parker et al. ............. 604/95.04 |
| 2010/0070008 A1 * | 3/2010 | Parker et al. ............. 607/116 |
| 2010/0262214 A1 * | 10/2010 | Robinson ............... 607/116 |
| 2013/0116768 A1 * | 5/2013 | Rakos et al. ............. 623/1.2 |

* cited by examiner

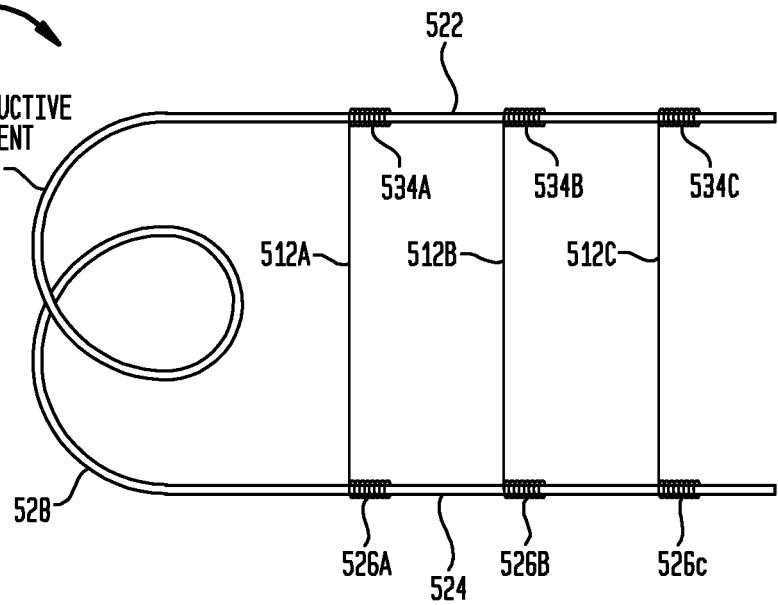
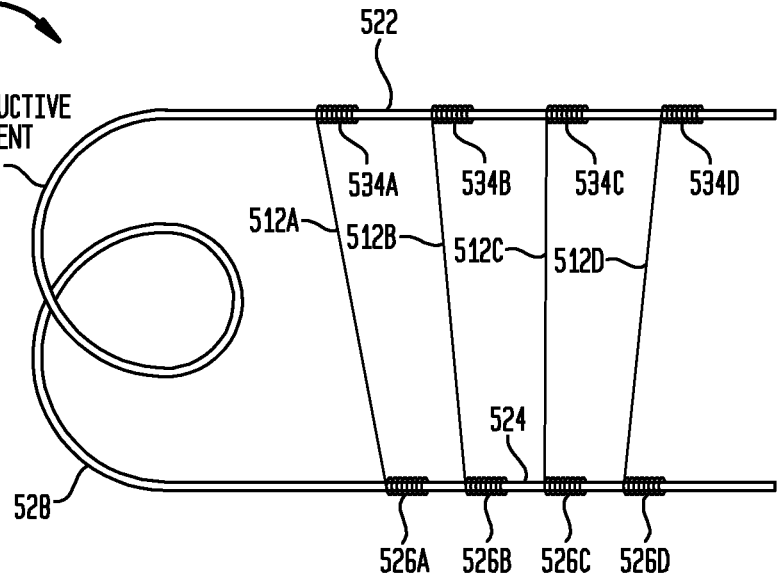

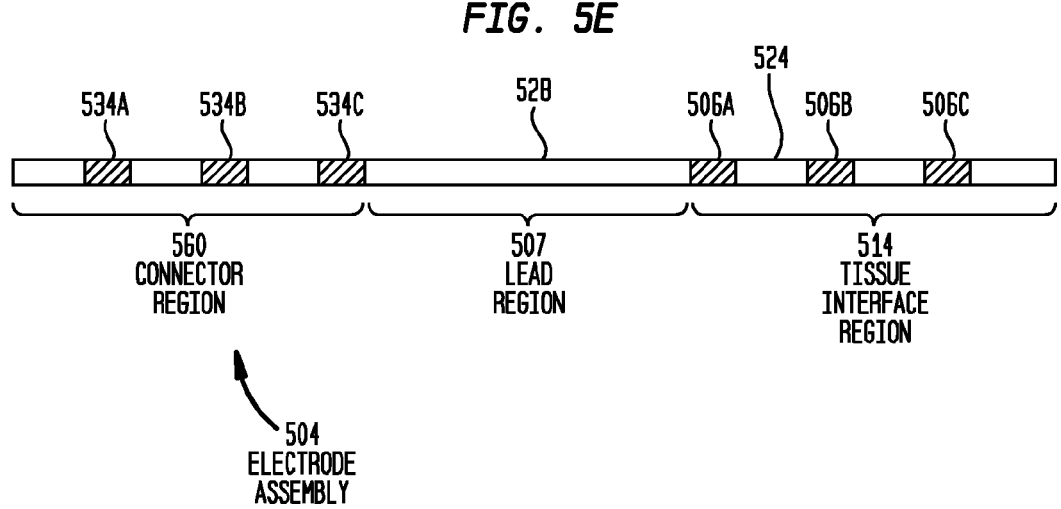

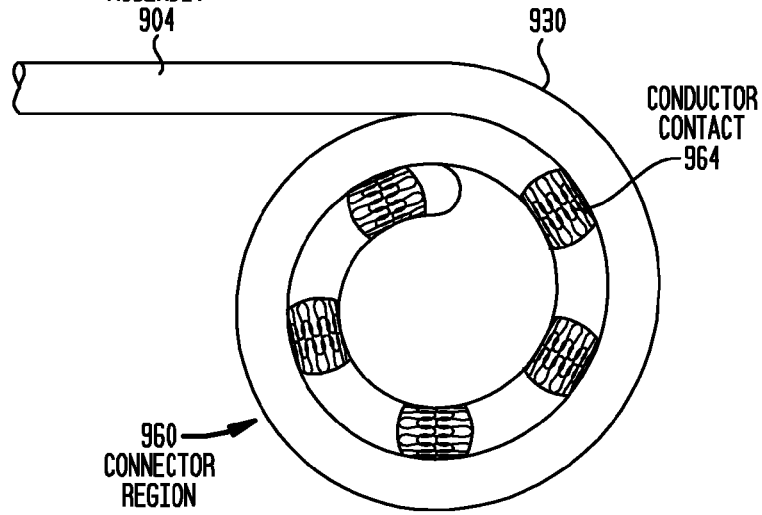
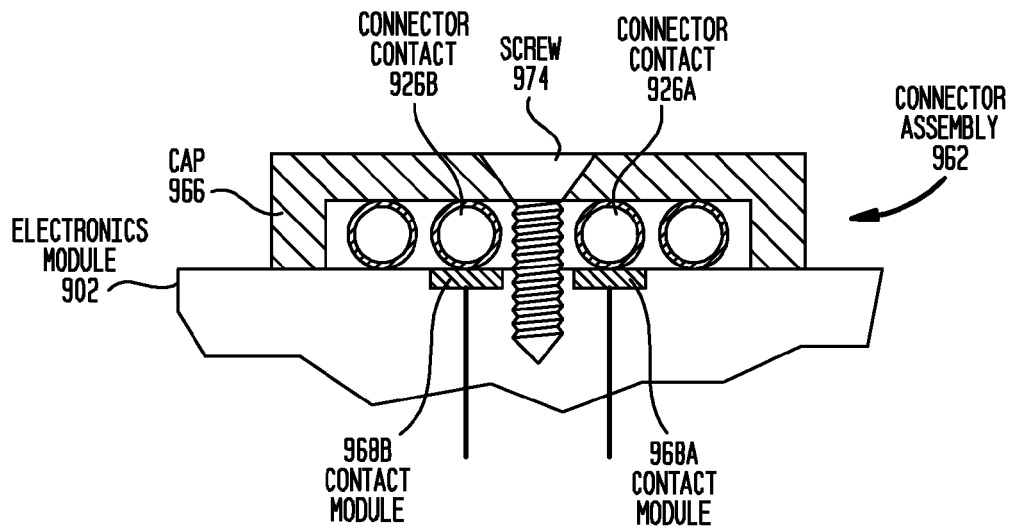

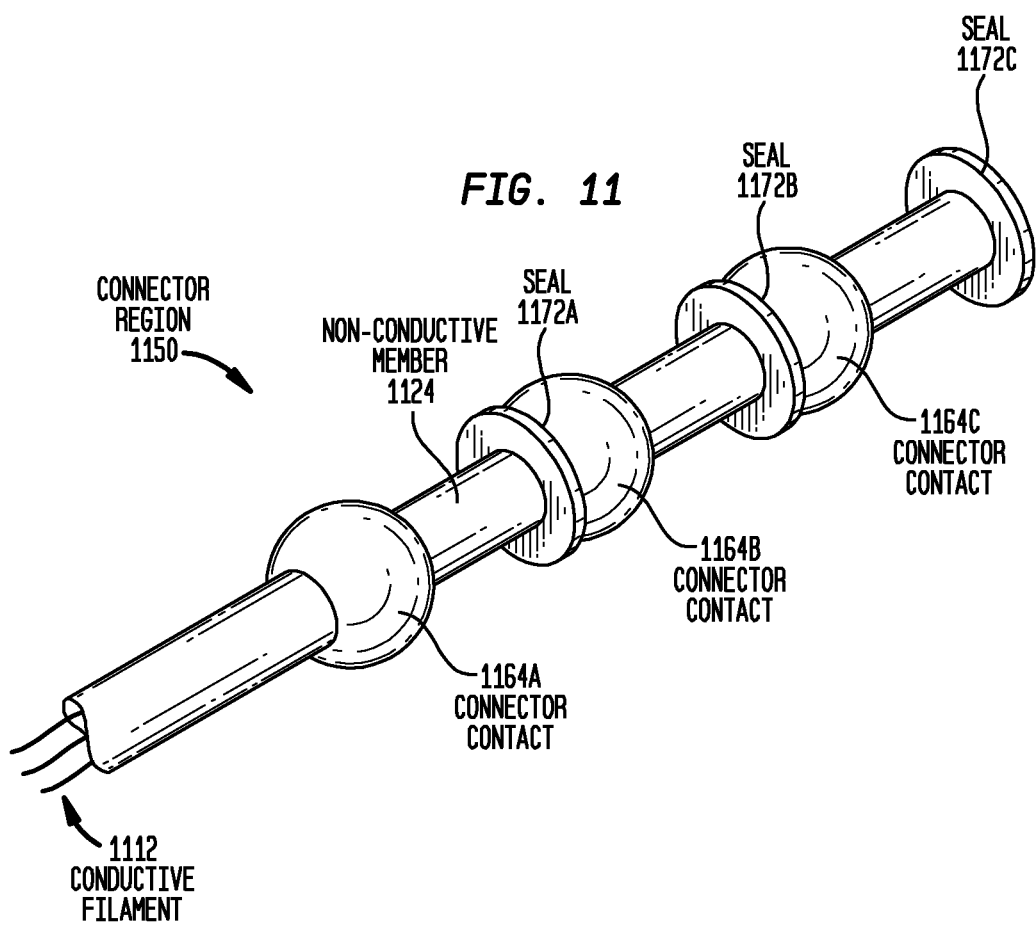

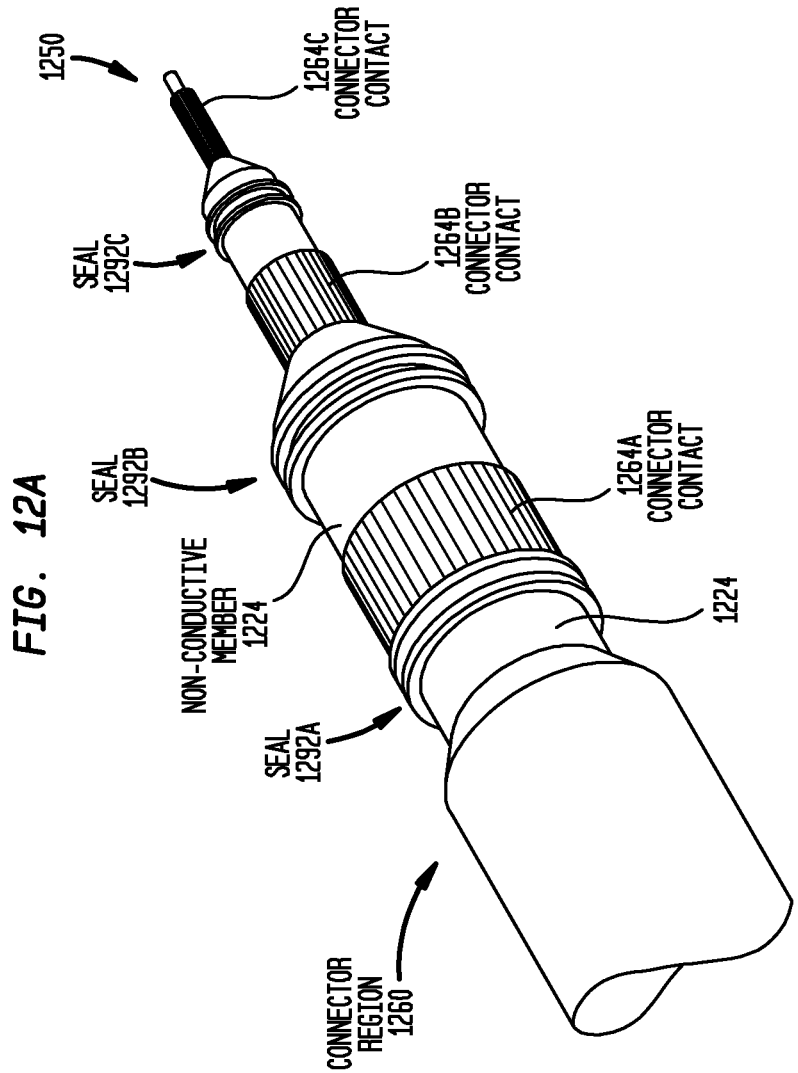

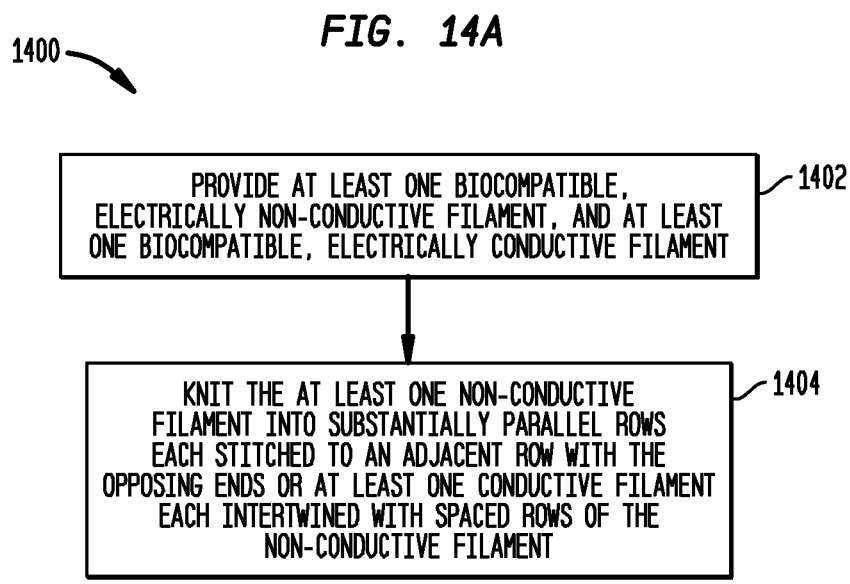

KNITTED ELECTRODE ASSEMBLY AND INTEGRATED CONNECTOR FOR AN ACTIVE IMPLANTABLE MEDICAL DEVICE

CROSS-REFERENCE TO RELATED APPLICATION

The present application claims priority from Australian Provisional Patent Application No. 2008904838, filed Sep. 17, 2008, Australian Provisional Patent Application No. 2009901534, filed Apr. 8, 2009, and Australian Provisional Patent Application No. 2009901531, filed Apr. 8, 2009, which are hereby incorporated by reference herein.

The present application is related to commonly owned and co-pending U.S. Utility Patent Applications entitled "Knitted Electrode Assembly For An Active Implantable Medical Device," filed Aug. 28, 2009, "Knitted Catheter," filed Aug. 28, 2009, "Bonded Hermetic Feed Through For An Active Implantable Medical Device," filed Aug. 28, 2009, "Stitched Components of An Active Implantable Medical Device," filed Aug. 28, 2009, and "Electronics Package For An Active Implantable Medical Device," filed Aug. 28, 2009, which are hereby incorporated by reference herein.

BACKGROUND

1. Field of the Invention

The present invention relates generally to active implantable medical devices (AIMDs), and more particularly, to a knitted electrode assembly and integrated connector for an AIMD.

2. Related Art

Medical devices having one or more active implantable components, generally referred to herein as active implantable medical devices (AIMDs), have provided a wide range of therapeutic benefits to patients over recent decades. AIMDs often include an implantable, hermetically sealed electronics module, and a device that interfaces with a patient's tissue, sometimes referred to as a tissue interface. The tissue interface may include, for example, one or more instruments, apparatus, sensors or other functional components that are permanently or temporarily implanted in a patient. The tissue interface is used to, for example, diagnose, monitor, and/or treat a disease or injury, or to modify a patient's anatomy or physiological process.

In particular applications, an AIMD tissue interface includes one or more conductive electrical contacts, referred to as electrodes, which deliver electrical stimulation signals to, or receive signals from, a patient's tissue. The electrodes are typically disposed in a biocompatible electrically non-conductive member, and are electrically connected to the electronics module. The electrodes and the non-conductive member are collectively referred to herein as an electrode assembly.

SUMMARY

In accordance with one aspect of the present invention, an active implantable medical device (AIMD) is provided. The AIMD comprises: a knitted electrode assembly comprising: at least one biocompatible, electrically non-conductive filament arranged in substantially parallel rows each stitched to an adjacent row, and at least one biocompatible, electrically conductive filament having a first end intertwined with a first row of the at least one non-conductive filament, and a second end intertwined with a second row of the at least one non-conductive filament, wherein the first and second rows are spaced from one another.

In accordance with one aspect of the present invention, a knitted implantable electrode assembly is provided. The method comprises: providing at least one biocompatible, electrically non-conductive filament, and at least one biocompatible, electrically conductive filament; and knitting the at least one non-conductive filament into substantially parallel rows each stitched to an adjacent row with a first end of the at least one conductive filament intertwined with a first row of the at least one conductive filament and a second end intertwined with a second row of the at least one non-conductive filament, wherein the first and second rows are spaced from one another.

BRIEF DESCRIPTION OF THE DRAWINGS

Aspects and embodiments of the present invention are described herein with reference to the accompanying drawings, in which:

FIG. 5B is a top view of a composite conductive filament in accordance with embodiments of the present invention;

FIG. 5C is a top view of a composite conductive filament in accordance with embodiments of the present invention;

FIG. 5E is a schematic diagram illustrating an electrode assembly with integrated connector, in accordance with embodiments of the present invention;

FIG. 9A is a top view of a coiled connector region of a knitted electrode assembly in accordance with embodiments of the present invention;

FIG. 9B is a cross-sectional view of a connector assembly having the coiled connector region of FIG. 9A inserted therein in accordance with embodiments of the present invention;

FIG. 11 is a perspective view of a connector region of a knitted electrode assembly in accordance with embodiments of the present invention;

FIG. 12A is a perspective view of a connector region of a knitted electrode assembly in accordance with embodiments of the present invention;

FIG. 14A is a high level flowchart illustrating a method for manufacturing a knitted electrode assembly having an integrated connector in accordance with embodiments of the present invention;

DETAILED DESCRIPTION

Figure 1:
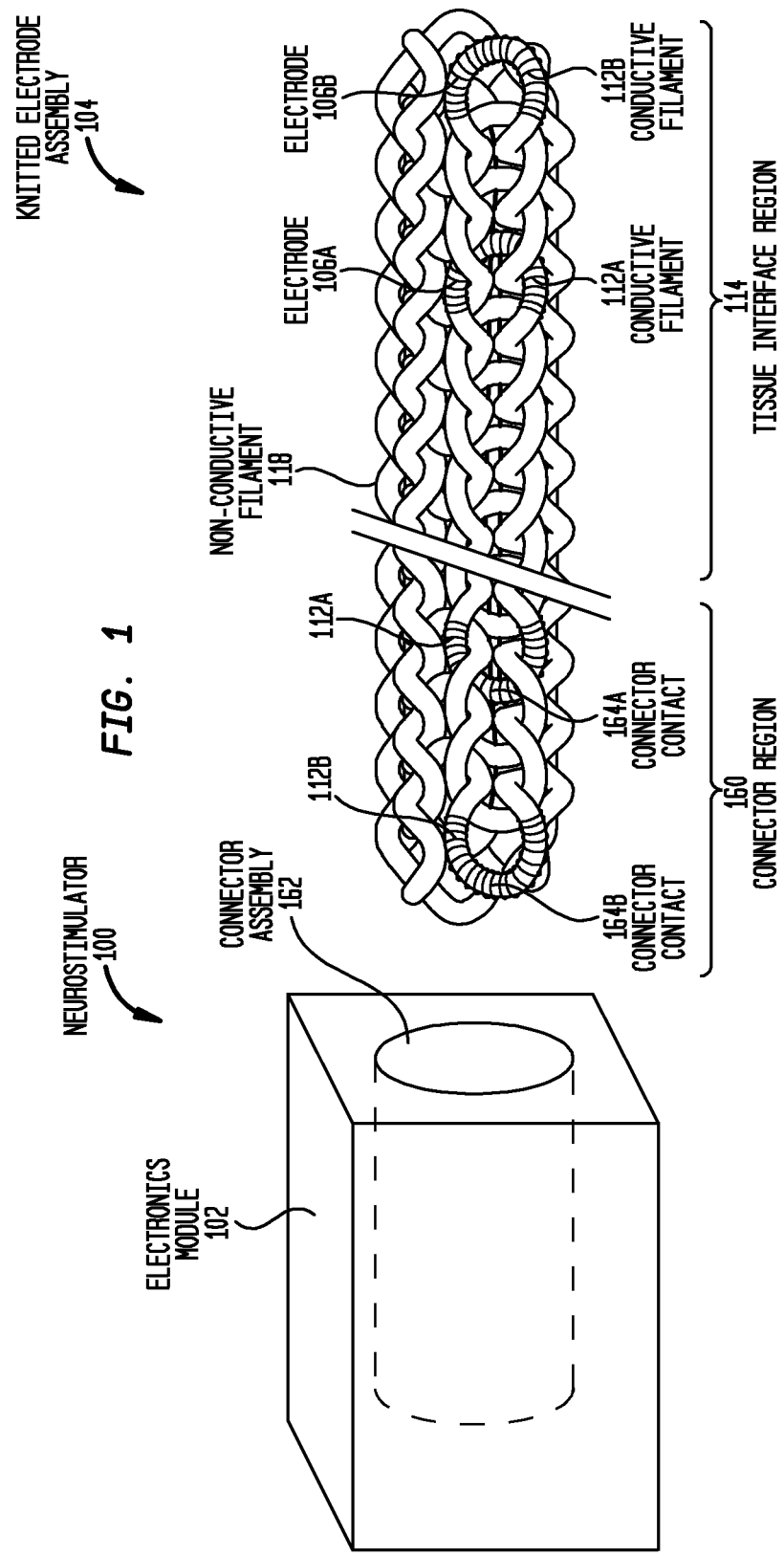
FIG. 1 is a perspective view of an exemplary active implantable medical device (AIMD), namely a neurostimulator, comprising a knitted electrode assembly in accordance with embodiments of the present invention.

Aspects of the present invention are generally directed to an active implantable medical device (AIMD) comprising an implantable, hermetically sealed electronics module and an electrode assembly formed using textile or fabric manufacturing methods.

A knitted electrode assembly in accordance with embodiments of the present invention has an electrical connector integrated therein that detachably electrically couples the electrode assembly to the electronics module. In particular, an electrode assembly in accordance with embodiments of the present invention comprises one or more biocompatible, electrically non-conductive filaments arranged in substantially parallel rows each stitched to an adjacent row. The electrode assembly also comprises at least one biocompatible, electrically conductive filament. The conductive filament has a first end intertwined with a first row of the at least one non-conductive filament, and a second end intertwined with a second row of the at least one non-conductive filament. The first and second rows are spaced from one another.

The AIMD electronics module includes a connector assembly having a module contact therein. The connector assembly is configured to be detachably coupled to the electrode assembly such that the module contact and the first intertwined end of the at least one conductive filament are electrically connected to one another. In certain embodiments, the connector assembly comprises a female receptacle to receive a section of the electrode assembly therein. In alternative embodiments, the connector assembly comprises a elongate male member configured to be inserted into a section of the electrode assembly.

Embodiments of the present invention are described herein primarily in connection with one type of AIMD, a neurostimulator, and more specifically a deep brain stimulator or spinal cord stimulator. Deep brain stimulators are a particular type of AIMD that deliver electrical stimulation to a patient's brain, while spinal cord stimulators deliver electrical stimulation to a patient's spinal column. As used herein, deep brain stimulators and spinal cord stimulators refer to devices that deliver electrical stimulation alone or in combination with other types of stimulation. It should be appreciated that embodiments of the present invention may be implemented in any brain stimulator (deep brain stimulators, cortical stimulators, etc.), spinal cord stimulator or other neurostimulator now known or later developed, such as cardiac pacemakers/defibrillators, functional electrical stimulators (FES), pain stimulators, etc. Embodiments of the present invention may also be implemented in AIMDs that are implanted for a relatively short period of time to address acute conditions, as well in AIMDs that are implanted for a relatively long period of time to address chronic conditions.

A knitted electrode assembly in accordance with embodiments of the present is not limited to devices that deliver electrical stimulation signals to a patient. For instance, in certain embodiments, the electrode assembly may be used to receive, record or monitor the physiological response of a patient's tissue to, for example, a therapy. In such embodiments, the electrodes receive a signal from the patient's tissue representing the physiological response. As described below, an electrode assembly of the present invention that delivers electrical stimulation signals to, or receives signals from, a patient's tissue may also include one or more other components, such as therapeutic agent delivery systems, sensors, etc., that interface with the patient's tissue. Knitted electrode assemblies are described in detail in commonly owned and co-pending U.S. Utility Patent Application entitled "Knitted Electrode Assembly For An Active Implantable Medical Device," filed Aug. 28, 2009. The content of this application is hereby incorporated by reference herein.

FIG. 1 is a perspective view of an active implantable medical device (AIMD), namely a neurostimulator 100, in accordance with embodiments of the present invention. Neurostimulator 100 comprises an implantable, hermetically sealed electronics module 102, and a tissue interface, shown as knitted electrode assembly 104. As described in greater detail below, knitted electrode assembly 104 comprises a biocompatible, electrically non-conductive filament arranged in substantially parallel rows each stitched to an adjacent row. In the illustrative embodiments of FIG. 1, the parallel rows form an elongate tubular structure. However, as described below, the plurality of parallel rows may be arranged to form electrode assemblies having different shapes and dimensions.

Electrode assembly 104 further comprises two biocompatible, electrically conductive filaments 112 intertwined with non-conductive filament 118. In the specific embodiments of FIG. 1, conductive filaments 112 are conductive threads, fibers, wires or other types of filament that are wound around sections of non-conductive filament 118 prior to the knitting process. Also as detailed below, the term composite conductive filament is used herein to refer to a non-conductive filament having a conductive filament wound around a section thereof. As detailed below, conductive filaments 112 may be intertwined with non-conductive filament 118 in one of several other manners.

In the embodiments of FIG. 1, a proximal or first end of each conductive filament 112 is wound around a proximal section of non-conductive filament 118. These first ends form connector contacts 164 which, as described below, electrically connect electrode assembly 104 to electronics module 102. A distal or second end of each conductive filament 112 is wound around a distal section of non-conductive filament 118. These ends of filament 112 form electrodes 106 which deliver electrical stimulation signals to, or receive signals from, a patient's tissue.

As noted, the term filament is used to refer to both the conductive and non-conductive threads, fibers or wires that are used to form knitted electrode assembly 104. It should be appreciated that, as shown in FIG. 1, filaments of varying diameters and properties may be used to form electrode assembly 104. As such, the use of filament to refer to both conductive and non-conductive elements should not be construed to imply that the conductive and non-conductive elements have the same diameter or properties.

As shown, knitted electrode assembly 104 comprises a connector region 160 and a tissue interface region 114. Connector region 160 comprises connector contacts 164, while tissue interface region 114 comprises electrodes 106. In certain embodiments of the present invention, connector region 160 and tissue interface region 114 are separated by a lead region (not shown) knitted from non-conductive filament 118. In these embodiments, conductive filaments 112 extend through the interior of the lead region between connector contacts 164 and electrodes 106.

FIG. 1 illustrates embodiments in which there is a one-to-one correspondence between connector contacts 164 and electrodes 106. It should be appreciated that in certain embodiments of the present invention a single connector contact 164 may be electrically connected to a plurality of electrodes 106. In certain such embodiments, a conductive filament 112 may be intertwined with non-conductive filament 118 at one location in connector region 160, but intertwined at several locations in tissue interface region 114. In alternative embodiments, a single electrode 106 may be electrically connected to a plurality of conductor contacts 164. In exemplary such embodiments, a conductive filament 112 may be intertwined with non-conductive filament 118 at one location in tissue interface region 114, but intertwined at several locations in connector region 160.

Electronics module 102 comprises a connector assembly 162 that is configured to mate with connector region 160 of knitted electrode assembly 104. In the illustrative embodiments of FIG. 1, connector assembly 162 comprises an elongate receptacle configured to detachable receive connector region 160 therein. When connector region 160 is inserted into connector assembly 162, connector contacts 164 are electrically coupled to module contacts (not shown) in connector assembly 162. The module contacts are electrically connected to other components of electronics module 102 through, for example, a feed through.

For ease of illustration, embodiments of the present invention will be primarily described with reference to embodiments in which connector assembly 162 is an elongate receptacle configured to receive connector region 160. It would be appreciated that in alternative embodiments, connector region 160 is formed in a tubular shape that is configured to receive an elongate connector assembly 162 extending from, or connected to, electronics module 102.

Figure 2:
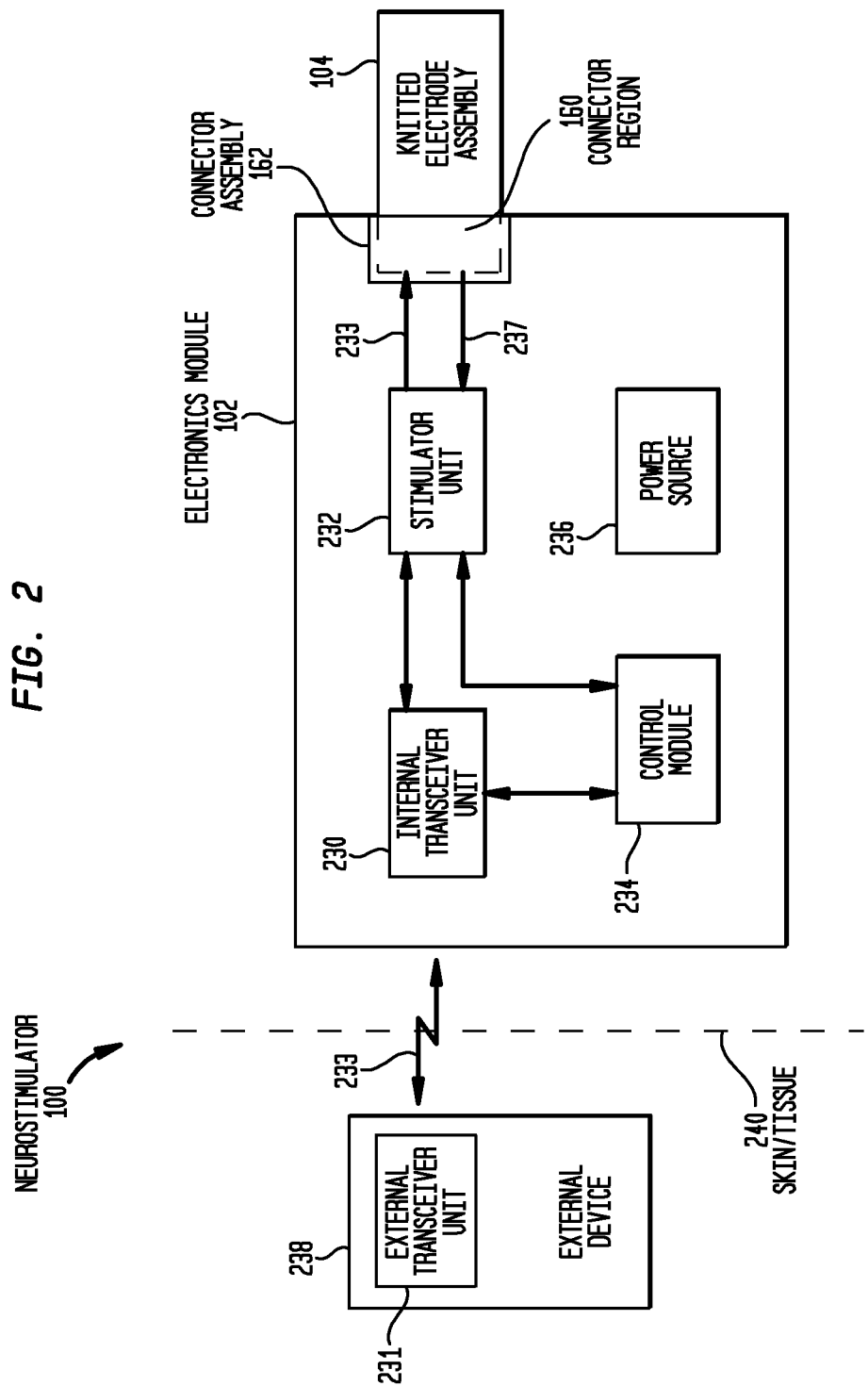
FIG. 2 is a functional block diagram of the neurostimulator illustrated in FIG. 1, in accordance with embodiments of the present invention.

FIG. 2 is a functional block diagram illustrating one exemplary arrangement of electronics module 102 of neurostimulator 100 of the present invention. In the embodiments of FIG. 2, electronics module 102 is implanted under a patient's skin/tissue 240, and cooperates with an external device 238. External device 238 comprises an external transceiver unit 231 that forms a bi-directional transcutaneous communication link 233 with an internal transceiver unit 230 of electronics module 102. Transcutaneous communication link 233 may be used by external device 238 to transmit power and/or data to electronics module 102. Similarly, transcutaneous communication link 233 may be used by electronics module 102 to transmit data to external device 238.

As used herein, transceiver units 230 and 231 each include a collection of one or more components configured to receive and/or transfer power and/or data. Transceiver units 230 and 231 may each comprise, for example, a coil for a magnetic inductive arrangement, a capacitive plate, or any other suitable arrangement. As such, in embodiments of the present invention, various types of transcutaneous communication, such as infrared (IR), electromagnetic, capacitive and inductive transfer, may be used to transfer the power and/or data between external device 238 and electronics module 102.

In the specific embodiment of FIG. 2, electronics module 102 further includes a stimulator unit 232 that generates electrical stimulation signals 233. Electrical stimulation signals 233 are provided to knitted electrode assembly 104 via the electrical connection between connector assembly 162 and connector region 160. Electrodes 106 (FIG. 1) of knitted electrode assembly 104 deliver electrical stimulation signals 233 to the patient's tissue. Stimulator unit 232 may generate electrical stimulation signals 233 based on, for example, data received from external device 238, signals received from a control module 234, in a pre-determined or pre-programmed pattern, etc.

As noted above, in certain embodiments, electrodes 106 of knitted electrode assembly 104 are configured to record or monitor the physiological response of a patient's tissue. In such embodiments, signals 237 representing the recorded response may be provided to stimulator unit 232 via connector assembly 162 for forwarding to control module 234, or to external device 238 via transcutaneous communication link 233.

In the embodiments of FIG. 2, neurostimulator 100 is a totally implantable medical device that is capable of operating, at least for a period of time, without the need for external device 238. Therefore, electronics module 102 further comprises a rechargeable power source 236 that stores power received from external device 238. The power source may comprise, for example, a rechargeable battery. During operation of neurostimulator 100, the power stored by the power source is distributed to the various other components of electronics module 102 as needed. For ease of illustration, electrical connections between power source 236 and the other components of electronics module 102 have been omitted. FIG. 2 illustrates power source 236 located in electronics module 102, but in other embodiments the power source may be disposed in a separate implanted location.

FIG. 2 illustrates specific embodiments of the present invention in which neurostimulator 100 cooperates with an external device 238. It should be appreciated that in alternative embodiments, deep brain stimulation 100 may be configured to operate entirely without the assistance of an external device.

Figure 3:
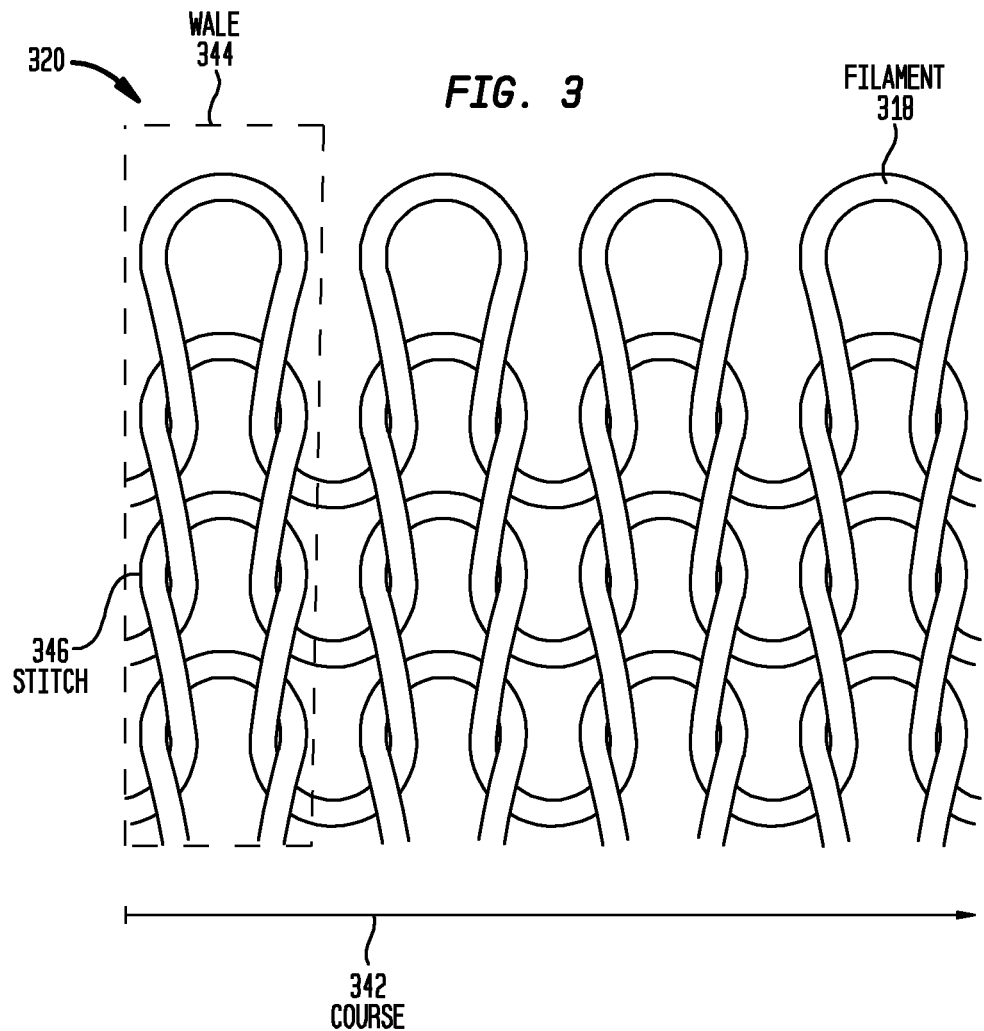
FIG. 3 is a perspective view of a section of a knitted member.

As noted above, embodiments of the knitted electrode assembly comprise at least one biocompatible, electrically non-conductive filament arranged in substantially parallel rows stitched to an adjacent row, with at least one biocompatible, electrically conductive filament intertwined with the non-conductive filament. Knitting is a technique for producing a two or three-dimensional structure from a linear or one-dimensional yarn, thread or other filament (collectively and generally referred to as "filaments" herein) to produce an intermeshed looped structure. A stitch in knitting includes the use of one or more loops to connect filaments to form the structure. There are two primary varieties of knitting, known as weft knitting and warp knitting. FIG. 3 is a perspective view of a section of a knitted structure 320 formed by weft knitting in a single filament 318.

As shown in FIG. 3, a filament course 342 is the generally meandering path of the filament, that creates substantially straight and parallel rows of filament loops. The filament course 342 is substantially perpendicular to the sequences of interlocking stitches 346. A sequence of stitches 346 is referred to as a wale 344. In weft knitting, the entire knitted structure may be manufactured from a single filament by adding stitches 346 to each wale 344 in turn. In contrast to the embodiments illustrated in FIG. 3, in warp knitting, the wales run roughly parallel to the filament course 342.

It should be appreciated that embodiments of the present invention may be implemented using weft or warp knitting. Furthermore, embodiments of the present invention may use circular knitting or flat knitting. Circular knitting creates a seamless tube, while flat knitting creates a substantially planar sheet.

Electrode assemblies in accordance with embodiments of the present invention may be knitted using automated knitting methods known in the art, or alternatively using a hand knitting process. It should be appreciated that the knitting method, filament diameter, number of needles and/or the knitting needle size may all affect the size of the stitches and the size of the resulting electrode assembly. As such, the size and shape of the assembly is highly customizable.

Figure 4A:
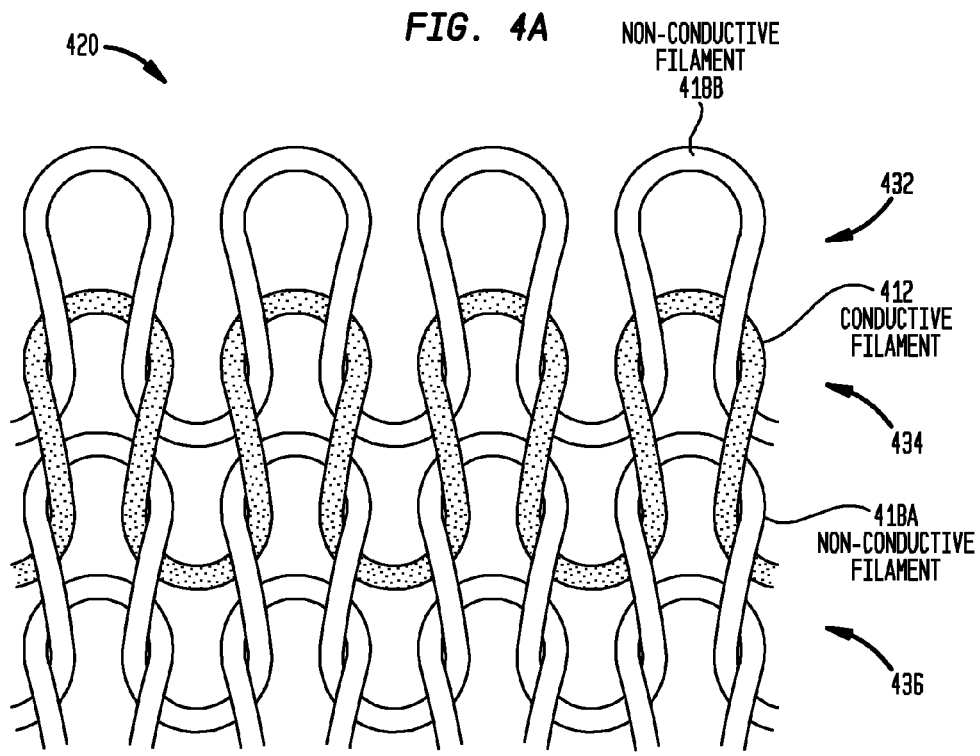
FIG. 4A is a perspective view of a section of a knitted electrode assembly in accordance with embodiments of the present invention.
Figure 4B:
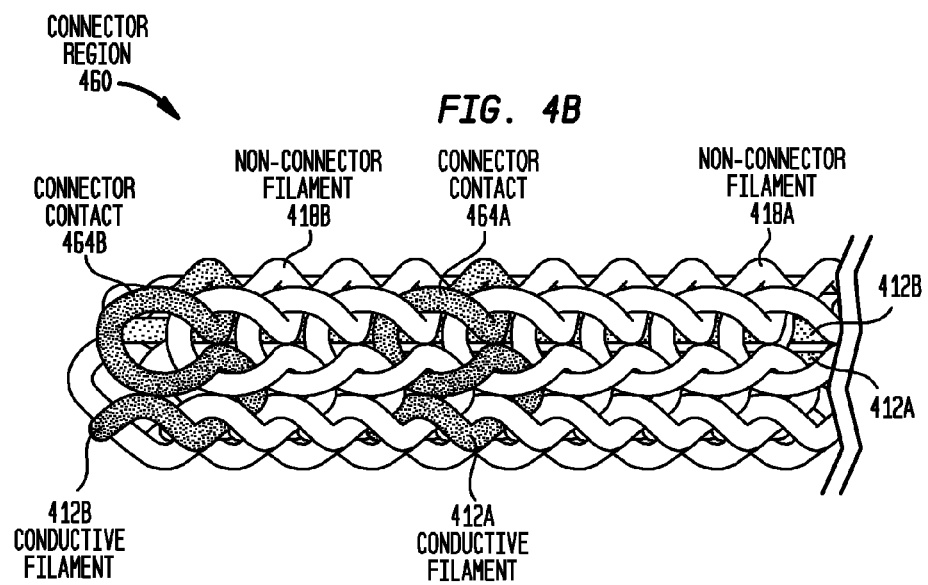
FIG. 4B is a side view of a connector region of a knitted electrode assembly in accordance with embodiments of the present invention.

FIGS. 4A and 4B illustrate embodiments of the present invention in which an electrode assembly is formed by alternately knitting with conductive and non-conductive filaments. A portion 420 of such a flat knitted structure is shown in FIG. 4A.

As shown in FIG. 4A, a first non-conductive filament 418A is knitted into a plurality of substantially parallel rows 436. A first conductive filament 412 is stitched to one of the rows 436 such that conductive filament 412 forms an additional row 434 that is parallel to rows 436. A second non-conductive filament 418B is stitched to row 434 such that the second non-conductive filament forms one or more rows 432 that are parallel to rows 434 and 436. For ease of illustration, a single conductive row 434 and a single non-conductive row 432 are shown. It should be appreciated that additional conductive or non-conductive rows may be provided in alternative embodiments. It should also be appreciated that in alternative embodiments each conductive row does not necessarily form a full row. For instance, a conductive filament could be used to form a number of stitches within a row, and a non-conductive filament could be used to complete the row.

FIG. 4B illustrates a connector region 460 of a circular knitted electrode assembly 404 in accordance with the structure of FIG. 4A. In the embodiments of FIG. 4B, a plurality of rows are knitted from a first non-conductive filament 418A and form a first section of connector region 460. A first conductive filament 412A forms a row that is knitted to the rows of non-conductive filament 418A. The row of first conductive filament 412A forms a connector contact 464A that may be, as described elsewhere herein, electrically connected to an electronics module.

In the embodiments of FIG. 4B, a second non-conductive filament 418B is knitted to the row of conductive filament 412A to form an additional non-conductive section of electrode connector region 460. A second conductive filament 412B forms a row that is knitted to the rows of non-conductive filament 418B. Similar to the row of conductive filament 412B, the row of second conductive filament 412B forms a connector contact 464B. As used herein, conductive filaments 412A and 412B are referred to as being intertwined with non-conductive filament 418B.

A variety of different types and shapes of conductive filaments may be used to knit an electrode assembly in accordance with embodiments of the present invention. In one embodiment, the conductive filament is a fiber manufactured from carbon nanotubes. Alternatively, the conductive filament is a platinum or other biocompatible conductive wire. Such wires may be given suitable surface treatments to increase their surface area (e.g. forming a layer of iridium oxide on the surface of platinum, utilizing platinum "blacking," or coating the wire with carbon nanotubes). In other embodiments, the conductive filament comprises several grouped strands of a conductive material. In other embodiments, the filament may be a composite filament formed from two or more materials to provide a desired structure. In certain such embodiments, the properties of the composite filament may change along the length thereof. For example, certain portions of the composite filament may be conductive, while portions are non-conductive. It would also be appreciated that other types of conductive filaments may also be used. Furthermore, although embodiments of the present invention are described using tubular or round fibers, it would be appreciated that other shapes are within the scope of the present invention.

As noted above, conductive filaments in accordance with embodiments of the present invention are intertwined with a non-conductive filament to form the electrode assembly. While a majority of the intertwined portion is an exposed conductive element, the remainder of the conductive filament may be insulated. In one such embodiment, a length of suitably insulated conductive filament (e.g. parylene coated platinum wire) is provided and the insulation is removed from the section that is to be intertwined, leaving the remainder of the filament with the insulated coating.

A variety of non-conductive filaments may be used to knit an electrode assembly in accordance with embodiments of the present invention. In one embodiment, the non-conductive filament is a biocompatible non-elastomeric polymer material. In another embodiment, the non-conductive filament is a biocompatible elastomeric material. For example, the elastomeric material may comprise, for example, silicone, silicone/polyurethane, silicone polymers, or other suitable materials including AORTech® and PBAX. Other elastomeric polymers that provide for material elongation while providing structural strength and abrasion resistance so as to facilitate knitting may also be used. It should be appreciated that other types of non-conductive filaments may also be used.

In a further embodiment, a non-conductive filament comprises a drug-eluting polymer. In such embodiments, drugs appropriate to the application may be incorporated into the structure so as to be automatically dispensed once the electrode assembly is implanted. In alterative embodiments, fibers may be coated with any of a number of materials that provide a therapeutic benefit. For example, in one embodiment the fibers may receive an anti-fibrogenic coating that prevents attachment to tissue. In other embodiments the fibers may be coated with a therapeutic material which promotes healing. In still further embodiments, the non-conductive filament comprises a thermo-softening plastic material, such as polypropylene. As described below, the thermo-softening plastic material allows the knitted structure to be formed into a variety of shapes using, for example, molding, sintering, etc.

Figure 5A:
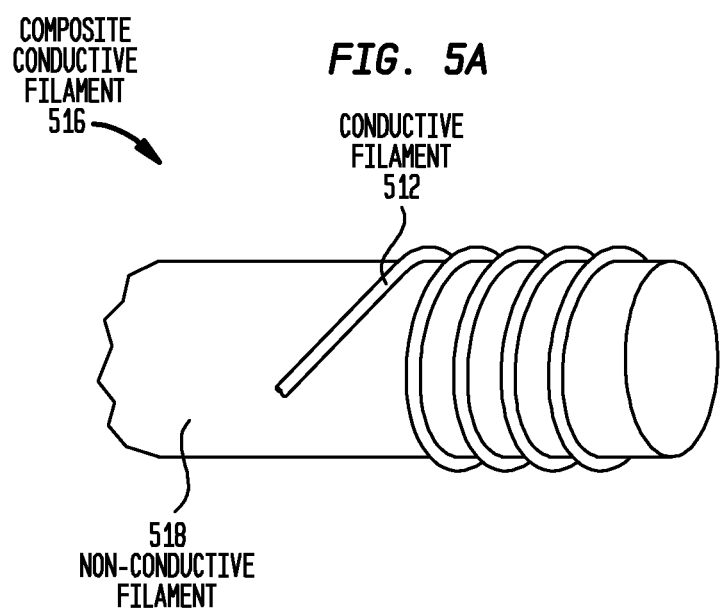
FIG. 5A is a perspective view of a composite conductive filament in accordance with embodiments of the present invention.

As noted above, in one embodiment of the present invention a composite conductive filament is used to form an electrode assembly. FIGS. 5A-5F illustrate such embodiments in greater detail. As shown in FIG. 5A, a composite conductive filament 516 is formed by winding sections of a conductive filament 512 around a non-conductive filament 518. Conductive filament 512 may be loosely or tightly wound onto non-conductive filament 518, and is referred to herein as being intertwined with non-conductive filament 518.

As noted, the term filament is used to refer to both the conductive and non-conductive threads, fibers or wires that are used to form a knitted electrode assembly. It should be appreciated that, as shown in FIGS. 5A-5F, filaments of varying diameters and properties may be used. As such, the use of filament to refer to both conductive and non-conductive threads, fibers and wires should not be construed to imply that the conductive and non-conductive elements have the same diameter or properties.

In certain embodiments of FIG. 5A, non-conductive filament 518 comprises a thermo-softening plastic material. The use of a thermo-softening filament allows conductive filament 512 to be wound around non-conductive filament 518 while the non-conductive filament is in a softened state. This ensures that conductive filament 512 is well integrated into non-conductive filament 518 so as to reduce any difference in the size of the stitches in the electrode area when compare to those in the non-conductive areas of a formed electrode assembly. As noted, conductive filament 512 may be loosely or tightly wound onto non-conductive filament 518. A loose winding provides integration of the two filaments and provides a compliant structure to manage fatigue. A tight winding provides substantially the same benefits, but also increases the amount of conductive filament in a single stitch. An alternative composite conductive filament is formed using a cording method as described in commonly owned and co-pending U.S. Utility Patent Application entitled "Knitted Electrode Assembly For An Active Implantable Medical Device," filed Aug. 28, 2009, the content of which is hereby incorporated by reference herein.

FIGS. 5B and 5C are top views of exemplary arrangements of composite conductive filament 516 of FIG. 5A. In the embodiments of FIGS. 5B, sections of three conductive filaments 512 are wound around non-conductive filament 518 to form composite conductive filament 516A. More specifically, a first end 534 of each conductive filament 512 is wrapped around a first section 522 of non-conductive filament 518. As described below, first ends 534 are positioned and spaced from one another such that when composite conductive filament 516A is knitted into an electrode assembly, first ends 534 will be spaced connector connectors.

Similarly, second end 526 of each conductive filament 512 is wrapped around a second section 524 of non-conductive filament 518. As described below, second ends 526 are positioned and spaced from one another such that when composite conductive filament 516A is knitted into an electrode assembly, second ends 526 will be spaced electrodes.

The embodiments of FIG. 5C are substantially the same as the embodiments of FIG. 5B except that four conductive filaments 512 are wound around non-conductive filament 518 to form composite conductive filament 516B. In the embodiments of FIG. 5C, the second ends 526 are shown positioned closer to one another than in the embodiments of FIG. 5B. As a result, a knitted electrode assembly formed from composite conductive filament 516B will have electrodes that are more closely spaced than the electrodes of a knitted electrode assembly formed from composite conductive filament 516A.

As described above, in certain embodiments of the present invention, connector contacts and electrodes of a knitted electrode assembly are spaced from another by a non-conductive region. In the illustrative embodiments of FIGS. 5B and 5C, this lead region may be formed from section 528 of non-conductive filament 518.

Figure 5D:
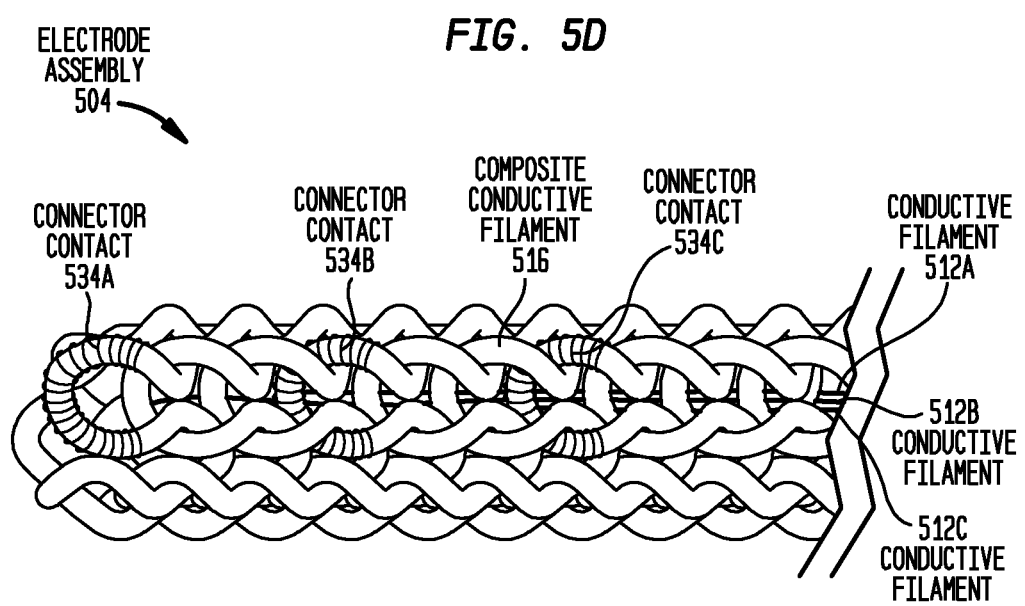
FIG. 5D is a side view of a connector region of a knitted electrode assembly in accordance with embodiments of the present invention.

FIG. 5D is a side view of a connector region 560 of a knitted electrode assembly formed from composite conductive filament 516. In these embodiments, electrode assembly 504 comprises an elongate tubular member. When connector region 560 is formed, the conductive portions of composite conductive filament 516 (i.e. the portions of conductive filaments 512 wound around non-conductive filament 518) form connector contacts 534. Conductive filaments 512 extend through the interior of the electrode assembly to electrodes (not shown).

FIG. 5E is a schematic diagram of an electrode assembly 504 formed using composite conductive filament 516A of FIG. 5B. For ease of illustration knitted electrode assembly 504 is shown schematically without the details of the conductive/non-conductive filaments and the knitted structure described elsewhere herein.

In these embodiments, filament 516A is circular knitted to form an elongate tubular structure. As shown, electrode assembly 504 comprises a connector region 560, a lead region 507, and a tissue interface region 514. Connector region 560 comprises section 522 of non-conductive filament 518 (FIG. 5B) having three connector contacts 534 formed therein from first ends 534 (FIG. 5B) of conductive filaments 512 (FIG. 5B). Tissue interface region 514 comprises section 524 of non-conductive filament 518 and three electrodes 506 formed from second ends 526 (FIG. 5B) of conductive filaments 512. Lead region 507 is formed from section 528 of non-conductive filament 518.

Figure 6A:
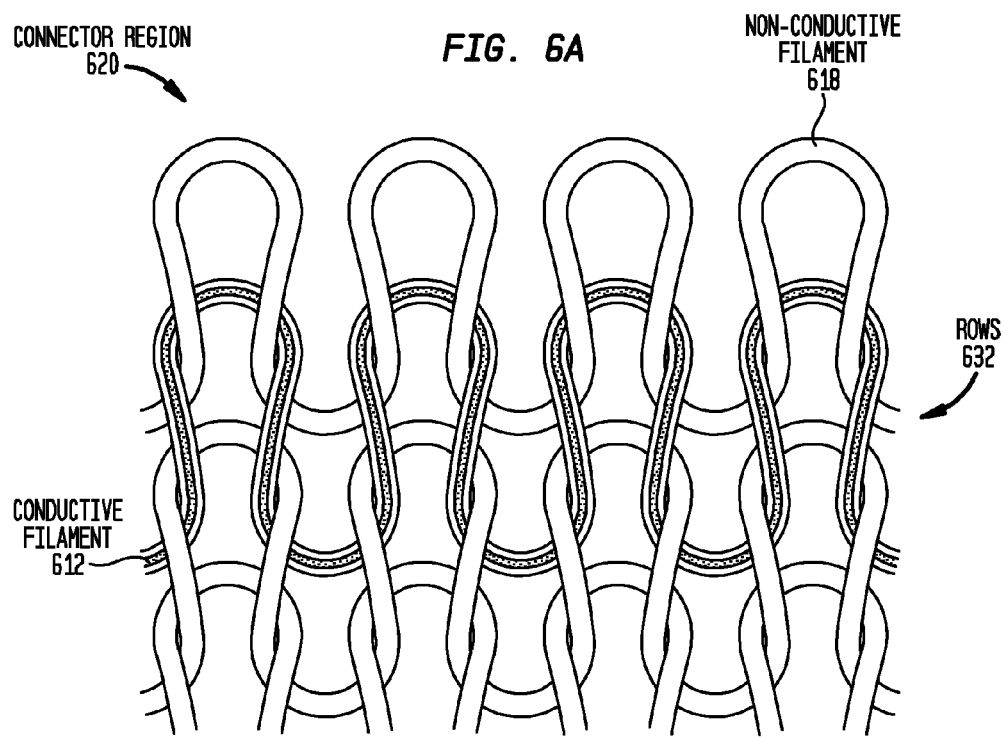
FIG. 6A is a perspective view of a section of a knitted electrode assembly in accordance with embodiments of the present invention.
Figure 6B:
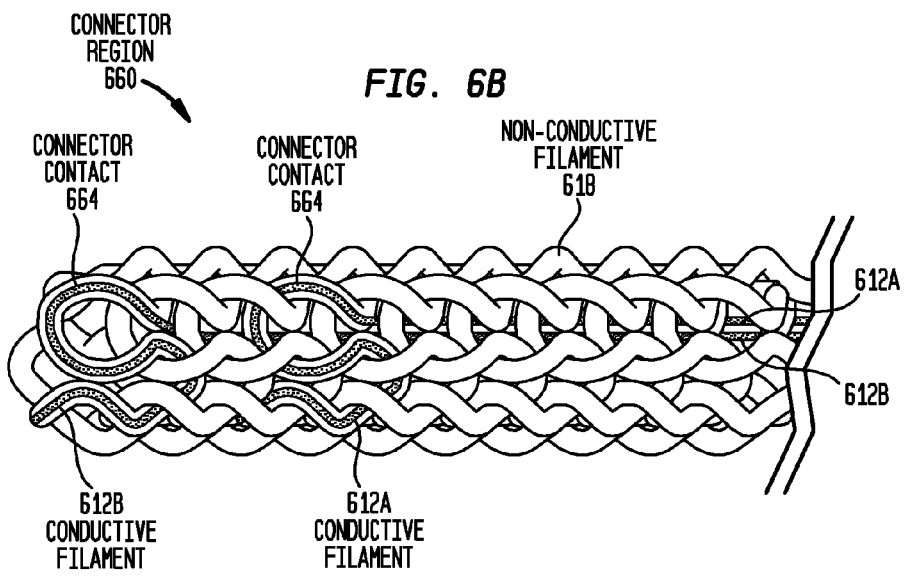
FIG. 6B is a side view of a section of a connector region of a knitted electrode assembly in accordance with embodiments of the present invention.

FIGS. 6A and 6B illustrate other embodiments of a knitted electrode assembly having at least one conductive filament intertwined with a non-conductive filament in accordance with aspects of the present invention. More specifically, FIGS. 6A and 6B illustrate embodiments of the present invention in which an electrode assembly is formed by concurrently knitting a conductive filament with a non-conductive filament.

FIG. 6A illustrates a portion of a flat knitted connector region 620. As shown, a non-conductive filament 618 is knitted into a plurality of parallel rows 632. A conductive filament 612 is concurrently knit with non-conductive filament 618 such that the conductive filament and the non-conductive filament 618 follow the same course. FIG. 6B illustrates a structure in which the parallel rows of non-conductive filament 618 form an elongate tubular structure.

In the embodiments of FIGS. 6A and 6B, conductive filaments 612 are concurrently knitted with a section of non-conductive filament 618 such that conductive filaments 612 follow the same course as the section of non-conductive filament 618. In this arrangement, conductive filaments 612 are positioned on the exterior surface of connector regions 620, 660. The concurrently knit sections of conductive filaments 612 are referred to as being intertwined with non-conductive filament 618. The intertwined portions of conductive filaments 612A, 612B each form connector contacts 664.

In the embodiments of FIG. 6B, the distal ends of conductive filaments 612A, 612B are also intertwined with non-conductive filament 618 in a tissue interface region (not shown). As such a section of the each filament 612 extends through the interior of connector region 660 to the tissue interface region.

Although FIGS. 6A and 6B illustrate embodiments in which the conductive filaments are positioned on the exterior surface of the knitted structure, it should be appreciated that in alternative embodiments the conductive filaments may in the interior of the electrode assembly. For example, if the electrode assembly is filled with a gel as described elsewhere herein, or is open to bodily fluids, an internal conductive surface may deliver electrical stimulation signals to the patient.

As noted above, FIGS. 4A-6B illustrated embodiments of the present invention in which a connector assembly is an elongate receptacle configured to receive a connector region therein. It would be appreciated that in alternative embodiments, the connector regions illustrated in FIGS. 4A-6B may have a tubular shape that is configured to receive an elongate connector assembly extending from, or connected to, an electronics module. In such embodiments, the connector contacts are disposed on the interior surface of the connector region so as to be electrically coupled to the connector assembly. In certain such embodiments, a tubular structure may be inserted within the interior of the connector region, and the tubular receives the elongate connector assembly therein. The tubular structure may have conductive and/or non-conductive portions.

Figure 7A:
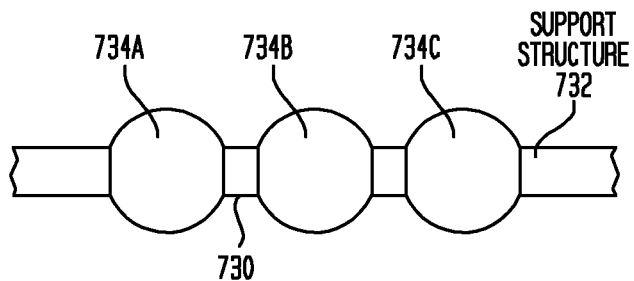
FIG. 7A is a side view of a support structure insertable into a connector region of a knitted electrode assembly, in accordance with embodiments of the present invention.
Figure 7B:
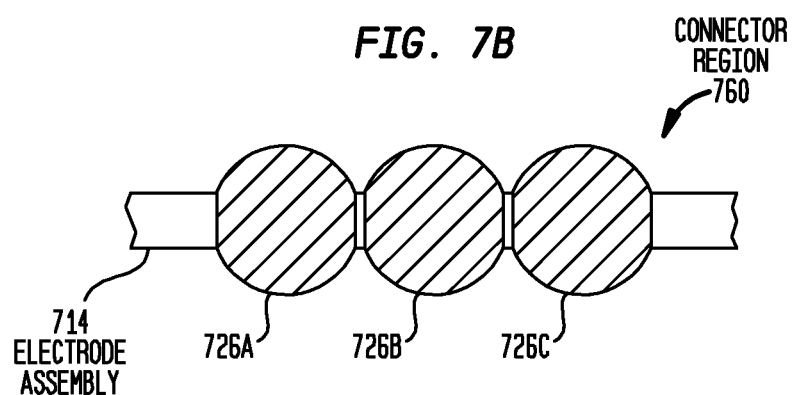
FIG. 7B is a side view of a connector region of a knitted electrode assembly having the support structure of FIG. 7A therein, in accordance with embodiments of the present invention.
Figure 7C:
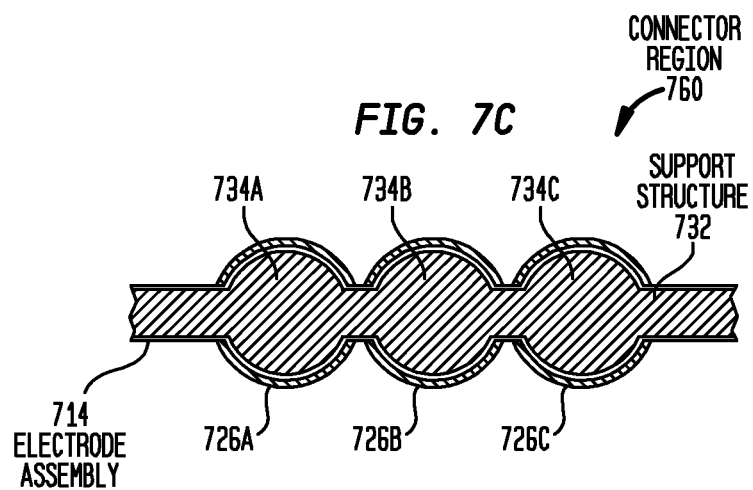
FIG. 7C is a cross-sectional view of a connector region of a knitted electrode assembly having the support structure of FIG. 7A therein, in accordance with embodiments of the present invention.

In certain embodiments of the present invention, sections of a knitted electrode assembly may be formed into a variety of different shapes during, or following the knitting process. FIGS. 7A-7C illustrate embodiments of the present invention in which a biocompatible support structure is used to shape a connector region of an electrode assembly into a desired shape. An exemplary support structure 732 is shown in FIG. 7A. Support structure 732 comprises an elongate tube 730 having three spherical shaped projections or bumps extending around the circumference thereof.

FIGS. 7B and 7C are perspective and cross-sectional views, respectively, of a connector region 760 of a knitted electrode assembly 714 having support structure 732 therein. For ease of illustration knitted electrode assembly 714 is shown schematically without the details of the conductive/non-conductive filaments and the knitted structure described elsewhere herein.

In the embodiments of FIGS. 7B and 7C, electrode assembly 714 is knitted about support structure 732 from one or more non-conductive filaments and one or more conductive filaments. The conductive and/or non-conductive filaments may be elastomeric or non-elastomeric. The conductive filaments and/or the non-conductive filaments are knitted under tension such that the knitted region takes the shape of the surface of support structure 732 following the release of the tension from the filaments. In other words, a tension is applied to one or more of the conductive filament and the non-conductive filament during the knitting process. When this tension is released, the filaments conform to the shape of support structure 732. As such, in the specific embodiments of FIGS. 7B and 7C, connector region has three regions 726 that project from the surface of electrode assembly 714. In these embodiments, regions 726 may be formed from conductive filaments, and regions 726 comprise connector contacts 726.

It would be appreciated that FIGS. 7A-7C illustrate one exemplary shaped support structure and resulting connector region 760. It would be appreciated that support structures having alternative shapes and dimensions may be utilized in embodiments of the present invention. For example, asymmetric shapes, tapered shapes, etc. may be employed as desired.

FIGS. 7B and 7C illustrate the insertion of a support structure into a connector region of an electrode assembly to form a connector region having a desired shape. It should be appreciated that a suitable support structure may be inserted into other regions of an electrode assembly. For instance, a support structure could be inserted into the tissue interface region and/or the lead region.

Figure 8A:
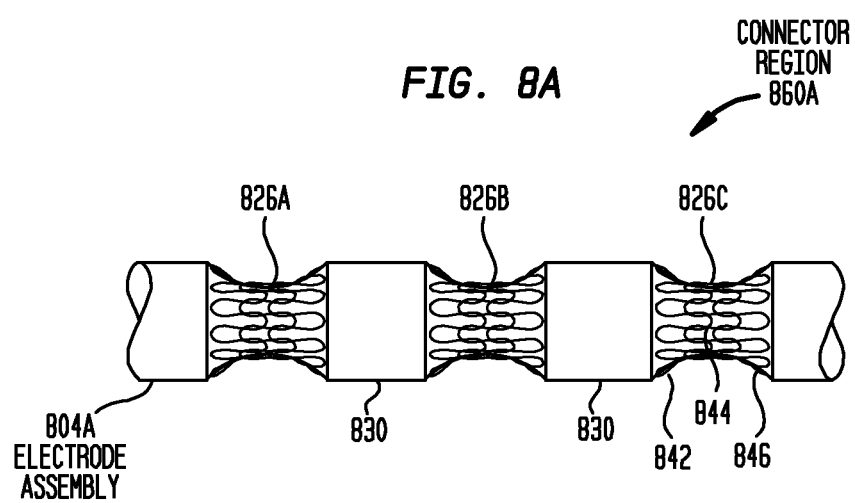
FIG. 8A is a side view of a section of a connector region of a knitted electrode assembly in accordance with embodiments of the present invention.
Figure 8B:
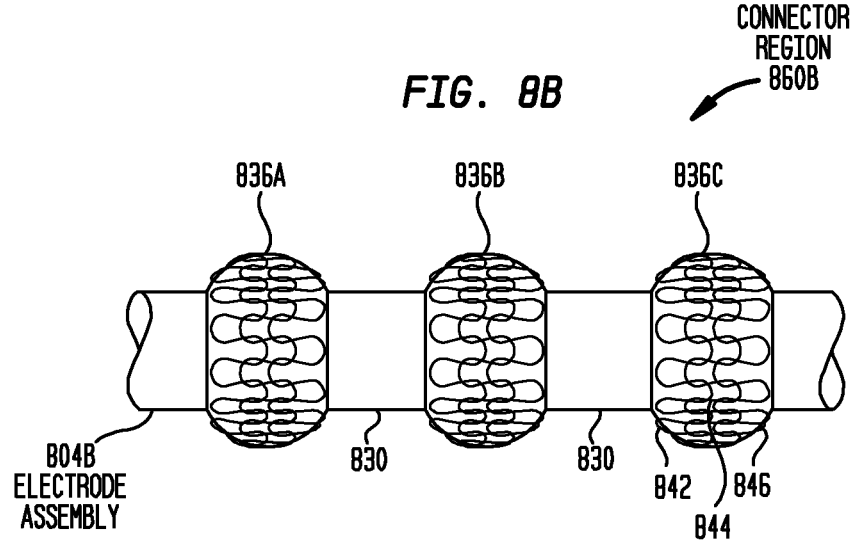
FIG. 8B is a side view of a section of a connector region of a knitted electrode assembly in accordance with embodiments of the present invention.

FIGS. 8A and 8B illustrate an alternative method for forming different shaped electrode assembly regions in accordance with embodiments of the present invention. In these embodiments, a connector region 860 of an elongate tubular electrode assembly 804 is formed by circular knitting one or more non-conductive and conductive filaments which, as described below, are knitted under varying tension. For ease of illustration, only sections 826 and 836 of connector regions 860 having conductive filament intertwined therein are shown in detail, and the solely non-conductive sections 830, are shown schematically.

As noted, in the embodiments of FIGS. 8A and 8B, non-conductive and/or the conductive filaments are placed under tension during the knitting process, and the tension is varied as rows are knitted. By varying the tension of the filament(s), the diameter of electrode assembly may be altered. For example, in the embodiments of FIG. 8A, the tension on the filament(s) is varied across sections 826. Specifically, the filament(s) are placed under a first tension when knitting row 846, a second greater tension when knitting row 844, and returned to the first tension during knitting of row 842. The increased tension creates an indentation in the surface of connector region 860A.

In contrast to the embodiments of FIG. 8A in which the tension placed on the filament(s) increases towards the center of sections 826, in the embodiments of FIG. 8B the tension placed on the filament(s) decreases towards the center of sections 836. Specifically, the filament(s) are placed under a first tension when knitting row 856, a second lower tension when knitting row 854, and returned to the first tension during knitting of row 852. The area of decreased tension forms a projection in the surface of connector region 860B.

It would be appreciated that the shapes illustrated in FIGS. 8A and 8B are merely illustrative, and that other shapes may be formed in accordance with embodiments of the present invention. Furthermore, it would be appreciated that embodiments may be implemented in which a support structure, as described above with reference to FIGS. 7B and 7B, is inserted into the electrode assembly during or following the knitting process described with reference to FIGS. 8A and 8B.

In embodiments of the present invention, the electrode assembly, or sections of the electrode assembly may be formed into a desired shape following the knitting process. Shaping the electrode assembly may facilitate coupling of a connector region with a connector assembly. FIG. 9A illustrates one such embodiment.

As shown, electrode assembly 904 is knitted into an elongate tubular shape and comprises a connector region 960. Connector region 960 has a plurality of conductor contacts 964 therein. For ease of illustration, only conductor contacts 964 are shown in detail, and the solely non-conductive sections 930, are shown schematically. In the embodiments of FIGS. 9A and 9B connector region 960 is formed into a plurality of concentric coils. Coiled connector region 960 is configured to mate with a connector assembly 962.

FIG. 9B is a cross-sectional view of connector region 960 and connector assembly 962. Connector assembly 962 comprises module contacts 968 positioned on the surface of electronics module 902. Connector contacts 964 are each configured to be positioned adjacent to a module contact 968 to electrically connect electrodes (not shown) of electrode assembly 904 to electronics module 902. Connector assembly 962 further comprises a cap 966 that uses screw 974 to force module contacts 968 and connector contacts 964 together. In alternative embodiments, pressure can be applied through the use of other mechanical means such as clips springs, etc.

Figure 10A:
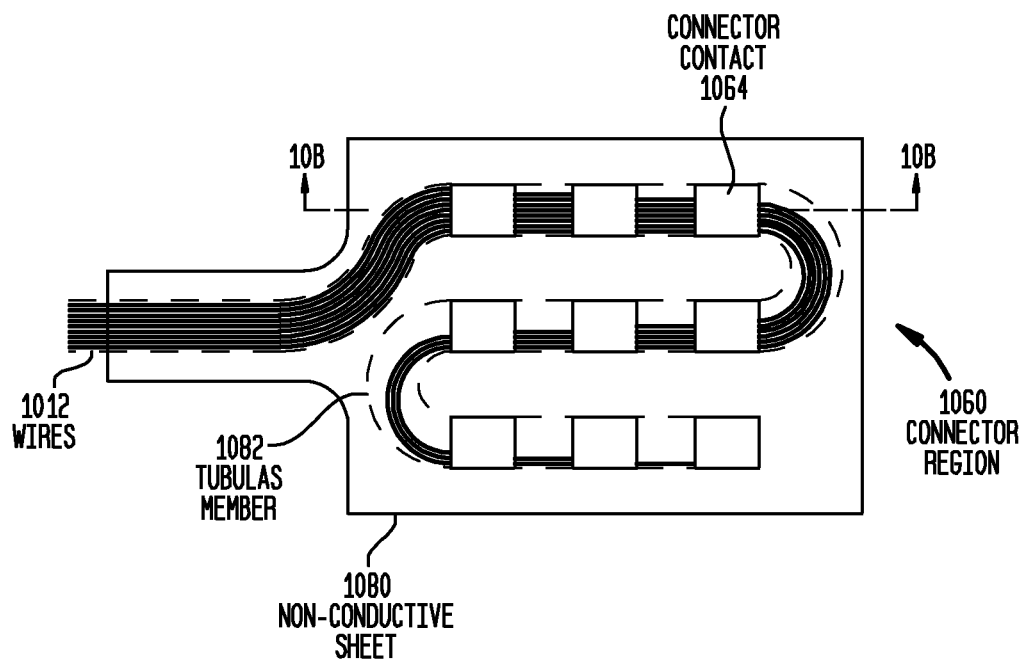
FIG. 10A is a top view of a connector region of a knitted electrode assembly in accordance with embodiments of the present invention.
Figure 10B:
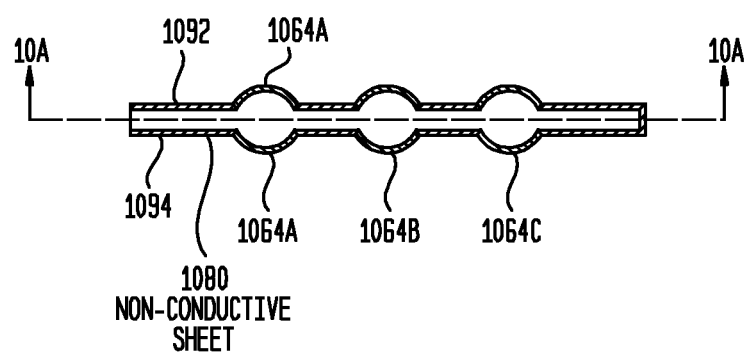
FIG. 10B is a cross-sectional view of a section of the connector region of FIG. 10B.

As noted above, an electrode assembly, or regions of an electrode assembly, in accordance with embodiments of the present invention may be formed into various shapes during or following the knitting process. FIGS. 10A and 10B are side and cross-sectional views, respectively, of a connector region 1060 formed into a substantially planar member following the knitting procedure. For ease of illustration, knitted components are shown schematically without the details of the knitted structure.

Connector region 1060 comprises a 3×3 array of conductor contacts 1064 fabricated from a knitted tubular member 1082. Tubular member 1082 may be knitted has described above, and has connector contacts 1064 thereon. Wires 1012 extend through member 1082 to electrodes (not shown). Tubular member 1082 is coiled into a serpentine path as shown in FIG. 10A to form the 3×3 array, and then the tubular member is over moulded with a non-conductive sheet 1080. Following the over moulding process, connector contacts 1064 remain exposed on at least one surface of sheet 1080. It would be appreciated that arrays of various sizes may be formed using embodiments of the present invention.

FIG. 10B is a cross-sectional view of connector region 1060 taken along line 10B-10B of FIG. 10A. For ease of illustration, FIG. 10B does not illustrate wires 1012, or tubular member 1080 embedded in non-conductive sheet 1080. As shown in FIG. 10B, connector contacts 1064 remain exposed on both opposing surfaces 1092, 1094 of sheet 1080.

In alternative embodiments of the present invention, a planar member such as shown in FIGS. 10A and 10B may be formed by using a thermo-forming non-conductive filament knitted into a tubular shape. In such embodiments, the tubular shaped electrode assembly would be thermo-formed into a flat sheet or other shapes following the knitting process.

In a still other embodiment, a planar structure may be formed using flat knitting. A flat knitted structure may be disposed over a three dimensional support structure to create raised contact points corresponding to the areas of connector contacts.

In further embodiments, the shape of an electrode assembly may be altered through sintering. For example, the structure may be laser sintered, and fiber crossing points within the structure may be formed into bending anisotropies. In other embodiments, an electrode assembly may be processed (via molding, sintering, etc.) to create inflexible portions, such as a stiffened tip, or to create, for example, anchoring barbs that may be used to secure the electrode assembly to the patient.

It would be appreciated that in alternative embodiments the electrode assembly is dipped into, or molded over by, a second material to form a desired shape or configuration. For example, one or more portions of the electrode assembly may be sealed with an added material to prevent the entry of body fluid into the structure. It would be appreciated that a number of different post-processing methods may be implemented to form the final structure.

In still further embodiments, following the knitting process an electrode assembly may be fully or partially covered by an outer structure, such as a tube. In such embodiments, the knitted structure would be stretched to reduce the width thereof, and the outer covering is placed over the desired portion. The knitted structure is then allowed to return to its previous non-stretched shape. The outer covering may be conductive, non-conductive or have both conductive and non-conductive sections, depending on the desired configuration. For example, an outer covering may be placed on the knitted structure such that conductive sections of the covering are disposed over the electrodes, while non-conductive sections extend over the other portions of the assembly. An outer structure may be beneficial to inhibit tissue growth into the knitted structure, to improve implantation by providing a smooth outer surface, to increase the surface area of conductive regions used to deliver electrical stimulation, increase stiffness of the assembly, etc.

As noted, in certain embodiments a cover may be disposed over, for example, the connector region of an electrode assembly to facilitate connection between the connector contacts and the module contacts are electrically connected. In alternative embodiments, a tubular structure may be inserted within the interior of the electrode assembly connector region. In such embodiments, the connector region forms a female member that is configured to receive a male connector assembly therein. In such embodiments, the interior of the electrode assembly may be filled with a biocompatible gel to ensure fluids do not enter the assembly.

In further embodiments of the present invention, a tube may extend partially or fully through the knitted structure. The tube may be used to, for example, receive a removable stylet that assists in the implantation of the electrode assembly.

FIG. 11 is a perspective view of a connector region 1150 of a knitted electrode assembly in accordance with embodiments of the present invention. In the embodiments of FIG. 11, knitted components are shown schematically without the details of the knitted structure.

Connector region 1150 comprises a knitted tubular non-conductive member 1124 knitted from one or more non-conductive filaments (not shown). Non-conductive member may be disposed on, or formed into, a solid fluid impermeable member. Extending about the surface of non-conductive member 1124 are connector contacts 1164. Connector contacts 1164 are similar to the embodiments of FIG. 8A and have a generally spherical shape. Connector contacts 1164 are formed from conductive filaments 1112. Conductive filaments 1112 extend through the interior of non-conductive member 1124 to electrodes (not shown).

In the embodiments of FIG. 11, connector region 1150 comprise a seal 1172 disposed between adjacent connector contacts 1164. As described in greater detail below, in these embodiments elongate connector region 1150 is configured to be received in an elongate receptacle, referred to herein as an elongate connector assembly. As such, connector region 1150 is designed such that, when inserted into the elongate connector assembly, the seals are designed to press against the inside of the receptacle to form a barrier preventing fluid travel between the regions of the connector contacts. Thus, seals 1172 prevent conductive fluid paths from forming between contacts. Seals 1172 may be separate elements that are moulded, glued or thermo-formed in desired locations along non-conductive member. It should be appreciated that certain embodiments utilize an insulated wire (e.g. parylene coated platinum wire) as conductive filaments. In such embodiments, the insulation is removed from the section of the wire which forms connector contacts 1164. As such, the remaining sections of wire remain insulated from the implant environment.

FIG. 12A is a perspective view of a connector region 1260 of a knitted electrode assembly in accordance with embodiments of the present invention. In the embodiments of FIG. 12A, knitted components are shown schematically without the details of the knitted structure.

Connector region 1260 comprises a knitted tubular non-conductive member 1224 knitted from one or more non-conductive filaments (not shown). Non-conductive member 1224 may be disposed on, or formed into, a solid fluid impermeable member. In these embodiments, the diameter of non-conductive member 1224 decreases toward the end 1250 of connector region 1260. Extending about the surface of non-conductive member 1224 are connector contacts 1264. Connector contacts 1264 are formed from conductive filaments (not shown).

In the embodiments of FIG. 12, connector region 1260 comprises a plurality of seals 1272 disposed between adjacent connector contacts 1264. As described in greater detail below, in these embodiments elongate connector region 1260 is configured to be received in an elongate receptacle, referred to herein as an elongate connector assembly. As such, connector region 1260 is designed such that, when inserted into the elongate connector assembly, the seals are designed to press against the inside of the receptacle to form a fluid barrier between connector contacts 1264. In other words, seals 1272 prevent fluid travel between the regions of the connector contacts and prevent conductive fluid paths from forming between contacts 1264. Seals 1272 may be separate elements that are moulded, glued or thermo-formed in desired locations along non-conductive member.

Figure 12B:
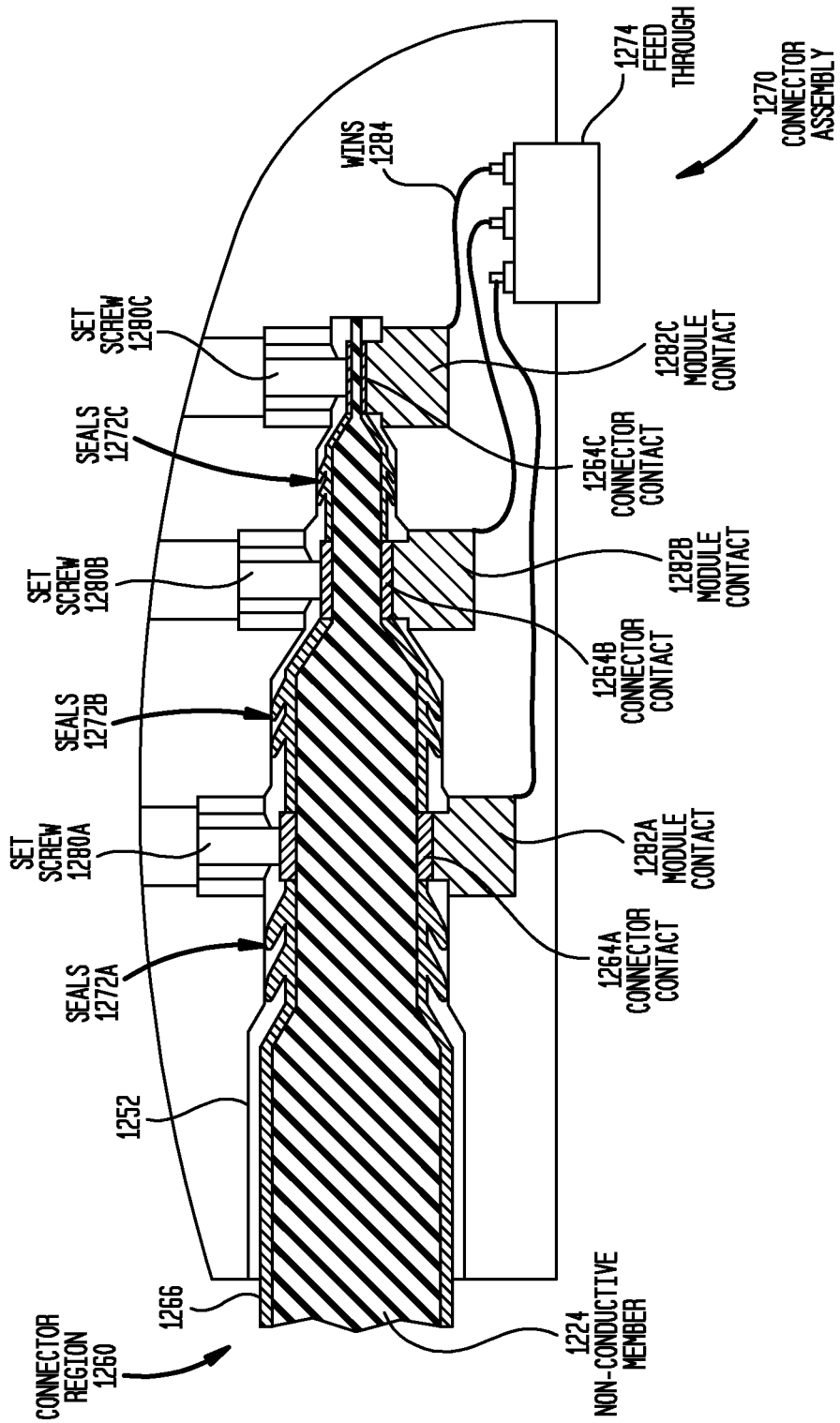
FIG. 12B is a cross-sectional view of a connector assembly having the connector region of FIG. 12A inserted therein, in accordance with embodiments of the present invention.

FIG. 12B is a cross-sectional view of a connector assembly 1270 having connector region 1260 of FIG. 12A inserted therein. Connector assembly 1270 comprises an elongate opening 1252 of an electronics module that is configured to mate with connector region 1260. Disposed on the inner surface of opening 1252 are module contacts 1282 to which connector contacts 1264 are electrically connected. Module contacts 1282 are electrically connected to a feed through 1274 that is electrically connected to one more hermetically sealed components of the electronics module. As shown, set screws 1280 may be used to ensure that an connector contacts 1264 and module contacts 1282 are in electrical contact with one another.

As previously noted with reference to FIG. 12A, connector region 1260 comprises a knitted non-conductive member 1224 that is thermo-formed such that the outer surface of the member is converted into a solid, fluid impermeable layer 1266. Disposed about layer 1266 between adjacent connector contacts 1264 are connector seals 1272. As shown, in the embodiments of FIG. 12B, two seals are provided between adjacent connector contacts 126.

When connector region 1264 is inserted into opening 1252, seals are designed to press against the inside of opening 1252 to form a fluid barrier that prevents the travel of fluid between connector contacts 1264. Thus, seals 1272 prevent conductive fluid paths from forming between contacts 1264.

Figure 13:
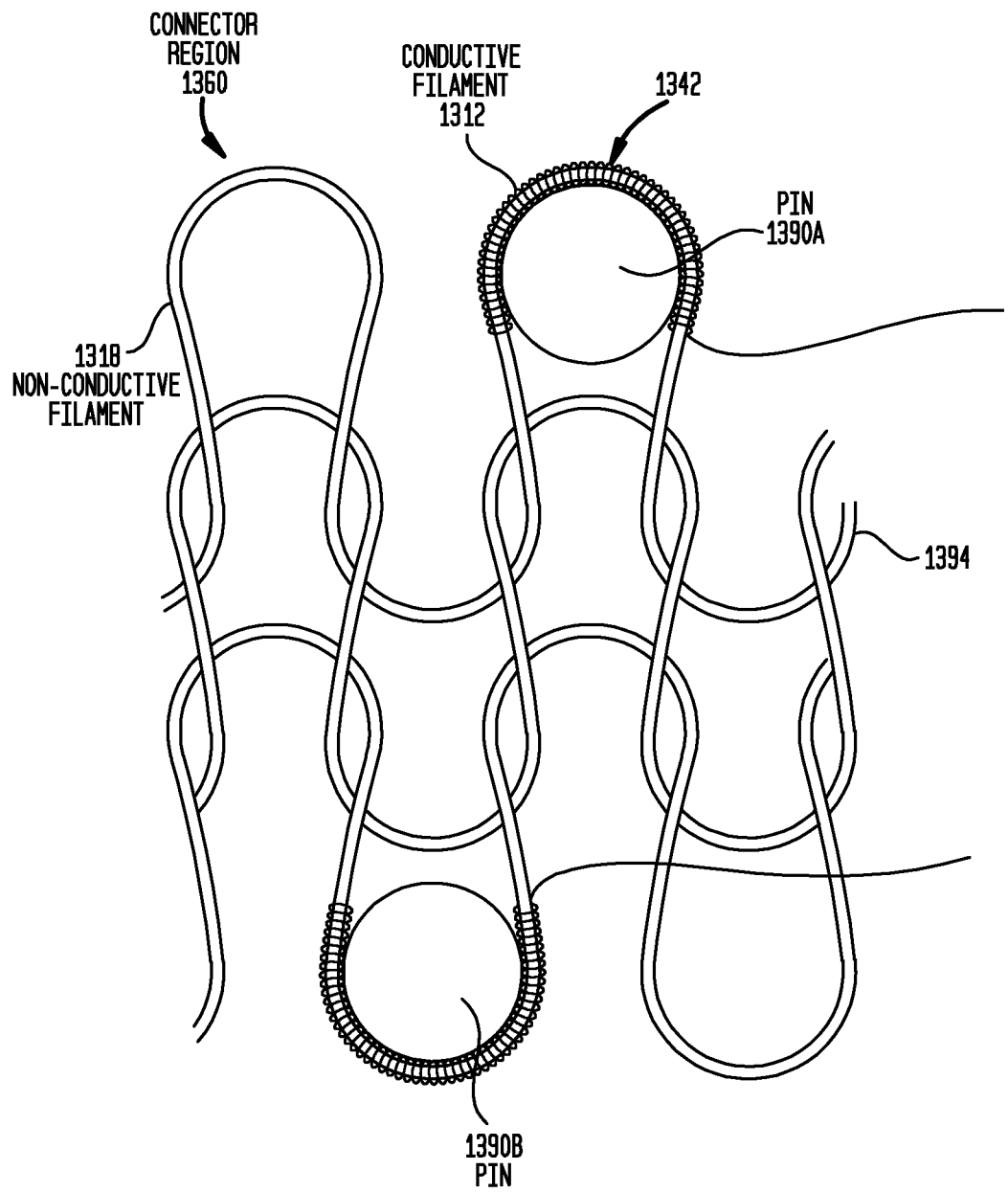
FIG. 13 is a top view of a section of a connector region of a knitted electrode assembly in accordance with embodiments of the present invention.

FIG. 13 illustrates an alternative connector region and connector assembly in accordance with embodiments of the present invention. In these embodiments, connector region 1360 comprises a knitted planar structure formed from non-conductive filament 1318. Conductive filaments 1312 are wrapped around loops 1342 of non-conductive filament 1318. In these embodiments, the connector assembly comprises a plurality of conductive pins 1390. Pins 1390 are inserted into loops 1342 having conductive filament 1312 wrapped there around to form an electrical connection between connector region 1360 and the connector assembly.

In certain embodiments, additional elements may be inserted into loops during the knitting process to form loops having a desired shape for connection with pins 1390. Formers can be inserted as the structure is knitted to form loops with a desired size and shape to interface with pins 1390.

It would further be appreciated that various patterns of pins may be used in embodiments of the present invention. For example, in certain embodiments, a radial pattern of pins may be formed to interface with contacts disposed about the circumference of a tubular structure. In alternative embodiments, a grid pattern may be formed to interface with connector contacts of a planar member.

FIG. 14A is a flowchart illustrating a method 1400 for manufacturing a knitted implantable electrode assembly in accordance with embodiments of the present invention. As shown, method 1400 begins at block 1402 where at least one biocompatible, electrical non-conductive filament, and at least one biocompatible, electrically conductive filament are provided. As noted above, numerous different types of non-conductive and conductive filaments may be provided. After the filaments have been provided, the method proceeds to block 1404 where the at least one non-conductive filament is knit into substantially parallel rows each stitched to an adjacent row. Opposing ends of the at least one conductive filament are intertwined with spaced rows of the non-conductive filament.

Figure 14B:
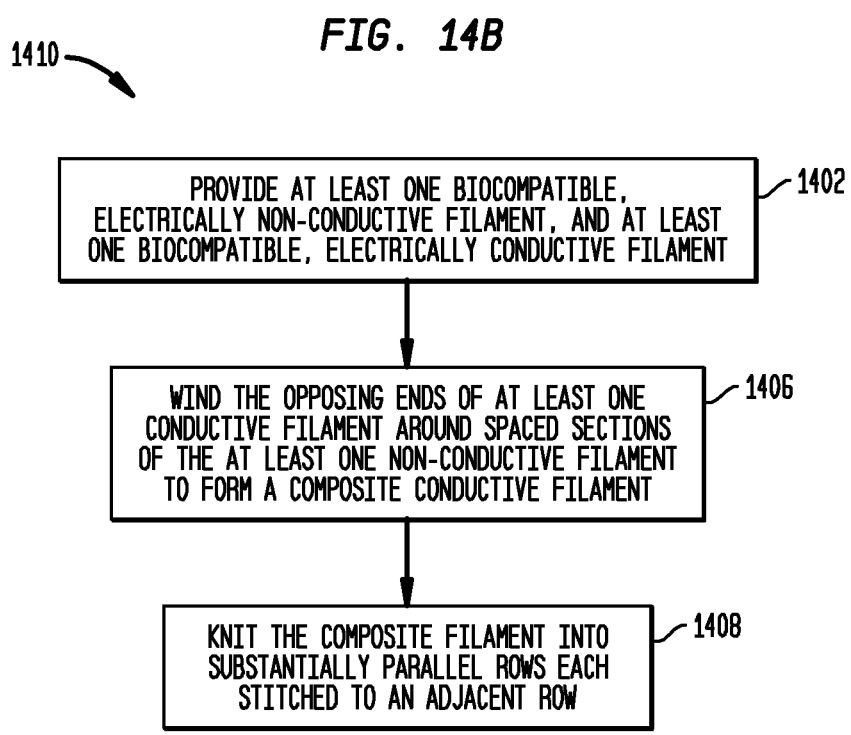
FIG. 14B is a detailed flowchart illustrating a method for manufacturing a knitted electrode assembly having an integrated connector in accordance with embodiments of the present invention.

FIG. 14B is a flowchart illustrating a variation of method 1400 of FIG. 14A, referred to as method 1410. Method 1410 begins at block 1402 where, as discussed above with reference to FIG. 14A, at least one biocompatible, electrical non-conductive filament, and at least one biocompatible, electrically conductive filament are provided. After the filaments have been provided, the method proceeds to block 1406 where opposing ends of the at least one conductive filament is wound around spaces sections of the at least one non-conductive filament to form a composite conductive filament. An exemplary composite conductive filament is described above with reference to FIGS. 5A-5C. At block 1408, the composite conductive filament is knit into substantially parallel rows, each stitched to an adjacent row.

Figure 14C:
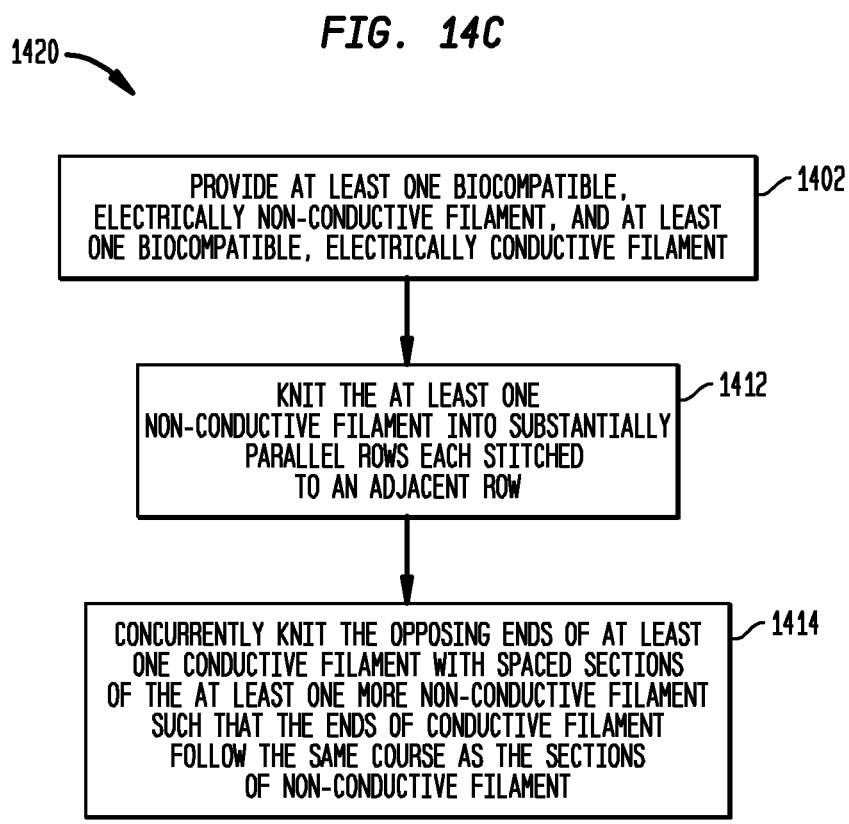
FIG. 14C is a detailed flowchart illustrating a method for manufacturing a knitted electrode assembly having an integrated connector in accordance with embodiments of the present invention.

FIG. 14C is a flowchart illustrating another variation of method 1400 of FIG. 14A, referred to as method 1420. Method 1420 begins at block 1402 where, as discussed above with reference to FIG. 14A, at least one biocompatible, electrical non-conductive filament, and at least one biocompatible, electrically conductive filament are provided. After the filaments have been provided, the method proceeds to block 1412 where the at least one non-conductive filament is knitted into substantially parallel rows, each stitched to an adjacent row. At block 1414 opposing ends of the conductive filament are knit with spaced sections of the at least one non-conductive filament. The ends of the conductive filament are concurrently knit with the sections of the at least one non-conductive filament such that the ends each follow the same course as the sections non-conductive filament.

As noted above, an electrode assembly in accordance with embodiments of the present invention may include electrodes for delivery of electrical stimulation signals to a patient. In certain embodiments, an electrode assembly is knitted from a non-conductive filament and has two or more conductive filaments extending there through. Disposed on the surface of the knitted electrode assembly are two electrodes formed by creating a ball or other shaped structure on the distal end of the conductive filaments. For example, in certain embodiments the conductive filaments comprise platinum wire that is inserted into the knitted structure such that distal structure mates with the non-conductive filament, and is held in the appropriate position. The distal structure may be formed by, for example, melting the distal end of the conductive filament with a localized heat source, by bunching the conductive filament into the desired shape, attaching a bulk material piece (e.g. platinum foil) having the desired shape to the conductive filament by weld, crimping or other method, etc. Such embodiments are illustrated in U.S. Utility Application entitled "Knitted Electrode Assembly For An Active Implantable Medical Device," filed Aug. 28, 2009, which is hereby incorporated by reference herein.

In certain embodiments of the present invention, a biocompatible gel may be disposed within a knitted electrode assembly. The gel may substantially fill the electrode assembly, or at least fill a number of stitches of the electrode assembly. It should be appreciated that a variety of suitable gels, such as silicone, may be used in embodiments of the present invention. In certain embodiments, the gel may act as a barrier to tissue ingrowth. In other embodiments the gel may provide or reinforce desirable mechanical properties of the knitted structure, such as adding stiffness. In still further embodiments, the gel is electrically non-conductive and functions to electrically separate connector contacts from one another and/or electrodes from one another. The inclusion of gel within a knitted structure is shown in commonly owned and co-pending U.S. Utility Patent Application entitled "Knitted Electrode assembly," filed Aug. 28, 2009, the contents of which are hereby incorporated by reference herein.

Further features and advantages of the present invention may be found in commonly owned and co-pending U.S. Utility Patent Applications entitled "Knitted Electrode Assembly For An Active Implantable Medical Device," filed Aug. 28, 2009, "Knitted Catheter," filed Aug. 28, 2009, "Bonded Hermetic Feed Through For An Active Implantable Medical Device," filed Aug. 28, 2009, "Stitched Components of An Active Implantable Medical Device," filed Aug. 28, 2009, and "Electronics Package For An Active Implantable Medical Device," filed Aug. 28, 2009, which are hereby incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A method for manufacturing a knitted implantable electrode assembly comprising:
    providing at least one biocompatible implantable, electrically non-conductive filament, and at least one biocompatible implantable, electrically conductive filament;
    winding first and second ends of a first of the at least one conductive filament around spaced sections of the at least one non-conductive filament; and
    knitting the at least one non-conductive filament having the conductive filament wound there around into an intermeshed looped structure having substantially adjacent parallel rows, each row stitched to an adjacent row with one or more loops, and the first end of the first of the at least one conductive filament intertwined with a first row of the at least one non-conductive filament to form a connector contact, and a second end of the first of the at least one conductive filament intertwined with a second row of the at least one non-conductive filament to form an electrode, wherein the first and second rows are spaced from one another and the connector contact and the electrode are spaced from one another by one or more third rows of the at least one non-conductive filament between the connecting contact and electrode.

2. The method of claim 1, wherein the at least one non-conductive filament consists of a single non-conductive filament, and wherein the method comprises:
    knitting the single non-conductive filament into substantially parallel rows each stitched to an adjacent row with the at least one conductive filament intertwined with the non-conductive filament.

3. The method of claim 1, further comprising:
    concurrently knitting the first and second ends of at least one conductive filament with first and second sections, respectively, of the at least one non-conductive filament such that the first and second ends each follow the same course as sections of at least one non-conductive filament, and wherein the first and second ends are positioned on the exterior surface of the electrode assembly.

4. The method of claim 1, wherein knitting the at least one non-conductive filament into the plurality of parallel rows comprises:
    circular knitting the at least one non-conductive filament into an elongate tube.

5. The method of claim 1, wherein knitting the at least one non-conductive filament into the substantially parallel rows comprises:
    flat knitting an electrode assembly having substantially planar dimensions.

6. The method of claim 1, further comprising:
    knitting one or more regions of the electrode assembly with one or more of the at least one conductive filament and the at least one non-conductive filament under varying tension.

7. The method of claim 1, further comprising:
    knitting at least one region of the electrode assembly about an elongate structure with one or more of the at least one conductive filament and the at least one non-conductive filament under tension such that the at least one region takes the shape of the surface of the elongate structure following the release of the tension from the one or more of the at least one conductive filament and the at least one non-conductive filament.

8. The method of claim 1, wherein providing the one or more non-conductive filaments comprises:
    providing at least one non-conductive filament comprising a thermo-softening plastic material.

9. The method of claim 8, further comprising:
    molding a region of the electrode assembly into a desired shape.

* * * * *